(12) United States Patent
Kuvshinov et al.

(10) Patent No.: US 7,495,148 B2
(45) Date of Patent: *Feb. 24, 2009

(54) DOUBLE RECOVERABLE BLOCK OF FUNCTION

(75) Inventors: Viktor Kuvshinov, Helsinki (FI);
Kimmo Koivu, Itasalmi (FI); Anne Kanerva, Itasalmi (FI); Andrei Anissimov, Helsinki (FI)

(73) Assignee: Unicrop Ltd, Helsinki (FI)

( * ) Notice: Subject to any disclaimer, the term of this patent is extended or adjusted under 35 U.S.C. 154(b) by 635 days.

This patent is subject to a terminal disclaimer.

(21) Appl. No.: 10/892,513

(22) Filed: Jul. 15, 2004

(65) Prior Publication Data
US 2005/0039229 A1    Feb. 17, 2005

Related U.S. Application Data

(63) Continuation-in-part of application No. 09/617,543, filed on Jul. 14, 2000, now Pat. No. 6,849,776.

(51) Int. Cl.
*C12N 15/82* (2006.01)
*C12N 15/55* (2006.01)
*A01H 1/02* (2006.01)

(52) U.S. Cl. .................. 800/271; 800/287; 800/288; 435/199; 435/320.1

(58) Field of Classification Search .............. None
See application file for complete search history.

(56) References Cited

U.S. PATENT DOCUMENTS 6,849,776 B1 *   2/2005  Kuvshinov et al. ......... 800/278

FOREIGN PATENT DOCUMENTS

| WO | WO97/44465 | 11/1997 |
| WO | WO02/06498 | 1/2002 |
| WO | WO03/076633 | 9/2003 |

OTHER PUBLICATIONS

Kuvshinov et al. Environmental Biosafety Research 4(2): 103-112 (Apr.-Jun. 2005).*
Kuvshinov et al. Plant Science 167(1): 173-182 (Jul. 2004).*
Kriete et al. The Plant Journal 9(6): 809-816 (1996).*
Williams, M.E. TIBTECH 13: 344-349 (Sep. 1995).*
U.S. Appl. No. 09/371,307, filed May 2, 2002, Brown et al.
Kuvshinov, Viktor; Koivu, Kimmo, Kanerva, Anne and Pehu, Eija Molecular control of transgene escape from genetically modified palnts. Plant Science 160 (2001) 517-522.
Kuvshinov , V, et al. 2005. Double recoverable block of function-. . . Environ, Biosafety res. E: 103-112.
Schernthaner, Control of seed germination in transgenic plants . . . PNAS vol. 100, No. 11; May 27, 2003, pp. 6855-6859.
Gressel, J. Tandenm constructs: preventing the rise of superweeds. TIBTECH 1999 (vol. 17) pp. 361-366.
Daniel, H. (2002) Molecular Strategies for gene containment in transgenic crops. Nature Biotechnology vol. 20 p. 581-586.

* cited by examiner

*Primary Examiner*—David T Fox
(74) *Attorney, Agent, or Firm*—Dodds & Associates; Susanne Somersalo; John Dodds

(57) ABSTRACT

An improved double Recoverable Block of Function (RBF) system for transgene containment with enhanced reliability is disclosed. The system includes two blocking constructs (BCs) at the opposite sides of a transgene of interest (TGI). The system comprises means for recovery of the function blocked by expression of the blocking genes of the BCs. The invention is also related to a kit comprising a cloning vector having the BCs and TGI or alternatively a place for TGI to be inserted in. Segregating (two-insert) and inducible (one-insert) types of double RBF are disclosed. The two BCs are either similar or different in their DNA and RNA structures. The two BCs may encode same protein but promoters driving the blocking genes are different and/or the coding sequence of the blocking genes is modified by codon preference change. A system comprising two BCs having different blocking genes is also disclosed. The system may consist of one or two Recovering constructs (RC), but also a system recovering without an RC is disclosed. Whether the system includes an RC or not, the recovery is induced by an external intervention that is controlled by human being.

19 Claims, 18 Drawing Sheets
(5 of 18 Drawing Sheet(s) Filed in Color)

5'UTR>>Start

CACAACCACAAGTATGGCACAAGTTATCAACACCTTTGATGGAGTTGCTGACTACCCTTCAGACATAACTACATCACCAAGTCTGAGCT
...AGTTAGTATGGCTCAAGTTATTAATACTTTTGATGGAGTTGCTGATTATCTTCAGACTTATCATCAAACTTCCAGATAATTATTACTAATTCGAAGCT

CAGGCTCTTGGATGGGTTGCTTCTAAGGGAAACCCTTGCTGATGTCGCTCGATGTGCTGATGTTCTGATATCTTCTCTAACAGGAGGGAAAGTTGC
CAAGCTCTTGGATGGGTTGCTTCTTCTAAGGAGAATCTTGCTGATGTTGCTGATGTTCTCCAGAGAAAATCTATTCGGAGGAGATATTTTTCAAATAGAGAGGAAAACTTC

CAGGAAAGTCTGGAAGGACCTGGAGGGAGGCTGATATCAACTACACACTCTGATAGAATCCTTTACTCTTCCGACTGGCTTATCTA
CAGGAAAATCTGGAAGAACATGGAGAGAAGCTGATATTAATTATACTTCTGGATTTAGAAATTCAGATGAATTCATCTGATTGCTTATTTA

CAAGACCACTGACCACTACCAGACCTTCACCAAGATCCGGTGAGAGACGCGCCCCTCGAGCTCGTTCAAACATTTGGCAATAAAGTTTCTTAAGATTGAAT
TAAACTACAGATCATTATCAAACTTTTACAAAAATTAGATAAATATTTGTGTTTTTGTATGTTGTGATCATTAATAAATAAATACATACCTCTT

Stop >> 3'UTR

CCTGTTGCCGGTCTTGCCGATGATTATCA...   *barnase1*
CTGCAGGCGCGGATCCCGTACGCCA   *barnase2*

Figure 5

Fig 7A, B and C

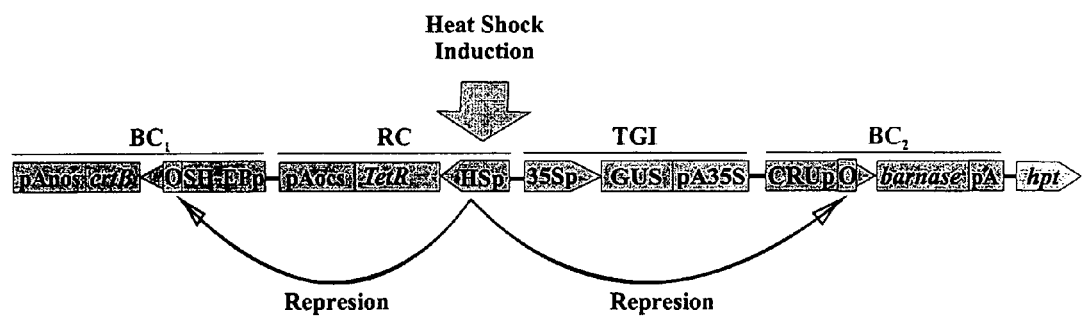
Figure 9 A and B

| Line of transgenic tobacco[1] | self pollinated or crossed | Heat shock treatment +/- | Germinated (%) | Ungerminated (%) | Proportions[2] G : U |
|---|---|---|---|---|---|
| pVK31 1 (HSp 2) | self pollinated | + HS | 100 | 0 | ∞ : 0 |
| pVK31 1 (HSp 2) | self pollinated | - HS | 0 | 100 | 0 : ∞ |
| pVK31 1 (HSp 2) | x NTS[3] | + HS | 97.5 | 2.5 | 40 : 1 |
| pVK31 1 (HSp 2) | x NTS | - HS | 0.8 | 99.2 | 1 : 100 |
| pVK31 5 (HSp 10) | self pollinated | + HS | 95 | 5 | 20 : 1 |
| pVK31 5 (HSp 10) | self pollinated | - HS | 0 | 100 | 0 : ∞ |
| pVK31 5 (HSp 10) | x NTS | + HS | 72 | 28 | 3 : 1 |
| pVK31 5 (HSp 10) | x NTS | - HS | 49 | 51 | 1 : 1 |

Figure 15

| Line of transgenic tobacco[1] | self pollinated or crossed | Germinated (%) | Ungerminated (%) | Proportions[2] G : U |
|---|---|---|---|---|
| pVK31 1 (35Sp 5) | self pollinated | 96 | 4 | 25 : 1 |
| pVK31 1 (35Sp 5) | x NTS | 91 | 9 | 10 : 1 |
| pVK31 3 (35Sp 6) | self pollinated | 95 | 5 | 20 : 1 |
| pVK31 3 (35Sp 6) | x NTS | 88 | 12 | 7 : 1 |

Figure 16

SEQUENCE LISTING

<160> NUMBER OF SEQ ID NOS: 16

<210> SEQ ID NO 1
<211> LENGTH: 336

```
<212> TYPE: DNA
<213> ORGANISM: artificial
<220> FEATURE:
<223> OTHER INFORMATION: Bacillus amyloliquefaciens
<220> FEATURE:
<221> NAME/KEY: misc_feature
<222> LOCATION: (1)..(336)
<223> OTHER INFORMATION: Barnase 1 synthetic coding sequence

<400> SEQUENCE: 1
atggcacaag ttatcaacac ctttgatgga gttgctgact accttcagac ctaccataaa      60
cttccagata actacatcac caagtctgag gctcaggctc ttggatgggt tgcttctaag     120
ggaaaccttg ctgatgtcgc tccaggaaag tctatcggag gtgatatctt ctctaacagg     180
gagggaaagt tgccaggaaa gtctggaagg acctggaggg aggctgatat caactacacc     240
tctggattca ggaactctga tagaatcctt tactcttccg actggcttat ctacaagacc     300
actgaccact accagacctt caccaagatc cggtga                               336

<210> SEQ ID NO 2
<211> LENGTH: 336
<212> TYPE: DNA
<213> ORGANISM: artificial
<220> FEATURE:
<223> OTHER INFORMATION: Bacillus amyloliqufaciens
<220> FEATURE:
<221> NAME/KEY: misc_feature
<222> LOCATION: (1)..(336)
<223> OTHER INFORMATION: barnase 2  synthetic coding sequence

<400> SEQUENCE: 2
atggctcaag ttattaatac ttttgatgga gttgctgatt atcttcaaac ttatcataaa      60
cttccagata attatattac taaatctgaa gctcaagctc ttggatgggt tgcttctaaa     120
ggaaatcttg ctgatgttgc tccaggaaaa tctattggag agatattttt ttcaaataga     180
gaaggaaaac ttccaggaaa atctggaaga acatggagaa agctgatat taattatact      240 tctggattta gaaattcaga tagaattctt tattcatctg attggcttat ttataaaact     300
acagatcatt atcaaacttt tacaaaaatt agataa                               336

<210> SEQ ID NO 3
<211> LENGTH: 299
<212> TYPE: DNA
<213> ORGANISM: artificial
<220> FEATURE:
<223> OTHER INFORMATION: Bacillus amyloliquefaciens
<220> FEATURE:
<221> NAME/KEY: misc_feature
<223> OTHER INFORMATION: Plant adapted synthetic coding sequence of
      Barstar gene
<400> SEQUENCE: 3
cgcggatcct gatcatgaag aaggctgtta tcaacggtga gcaaattagg tctatctctg      60
atcttcacca gacccttaag aaggagcttg ctcttccaga gtactacgga gagaaccttg     120
atgctctatg ggattgcctt accggatggg tggagtaccc acttgttttg gagtggaggc     180
agtttgagca gtctaagcag cttactgaga atggagctga gagtgttctt caggttttcc     240
gggaggctaa ggctgaggga tgcgatatca ccatcattct ttcttgagag ctcgagcgc     299

<210> SEQ ID NO 4
<211> LENGTH: 1183
<212> TYPE: DNA
<213> ORGANISM: artificial
<220> FEATURE:
<223> OTHER INFORMATION: Brassica napus
```

<220> FEATURE:
<221> NAME/KEY: misc_feature
<223> OTHER INFORMATION: CRU prmoter with artificial polyadenlylation site

<400> SEQUENCE: 4

| | | | | | |
|---|---|---|---|---|---|
| cttctacacg | ttttgaaaag | ttaacctgtt | ggttaaatgg | ttagctatga | ctctcgcaac | 60 |
| aaacccaacc | cttaagatga | tgatggttta | acatttgaca | acatagttaa | gactgtgtct | 120 |
| atataatagt | caacaaattc | agattgtagt | attatggagt | caacatattt | cgagatcaaa | 180 |
| aacattcaaa | acgtaaatct | atcgacgtct | cacatagttt | tgttatgaag | ctgatgaaaa | 240 |
| aagttggaag | acatagtttt | gcaaacatca | tttgttgcta | acgtataaac | gttggtttga | 300 |
| ttaaatgtaa | taggataagg | atatccgttt | gttcatataa | ttgagttaaa | ttatattttg | 360 |
| gttattataa | tatgttaagt | tgaaaataaa | taggtccaac | aaccttgttt | aaatagattt | 420 |
| tttaggagtg | attccctttt | aatagtatag | attatactct | cttcctaatc | gaccttccgt | 480 |
| ggggtaaagt | ggtcaattat | attctttatg | gatgagcttg | attgagaatg | ggtttatggg | 540 |
| ttatgacaag | ggcatgtaca | aatgtcactg | cctcttgaca | tgcaaccgaa | cagttggcga | 600 |
| ctcaagtcgc | agaagataca | acggaccaaa | ccctccgagt | gtcgccgcgt | ctgttatgtg | 660 |
| tcacctttt | gtctccttc | cttaaaaatt | ggtaactcat | ttttcaaaaa | aagaagagga | 720 |
| tagttttggc | tgtatctcct | aaactattcg | atcacaacgc | cagatatttt | aatactggat | 780 |
| actagtgatg | taatttgatt | tgttaattgt | caaaaagtag | attctcctat | ctcgttttta | 840 |
| gttcaattat | tatatggtta | aatgaattta | agtcgattag | aaatgattag | ttaatcaacc | 900 |
| agagttgctc | tataagtcta | tactgataac | atgaaccatt | ttctaaaaat | gagatagata | 960 |
| catttgaatt | ttgtcgtggt | ttggagtatg | cggagatagt | cgtacgcgca | tgaacatcat | 1020 |
| gagacacttg | cttcagctca | cagagtgacg | tgtaaagacc | atagacccac | gacttcatgc | 1080 |
| aaacccattc | ctacgtggca | caaaccttca | tgctcactcc | acatatataa | actcctacca | 1140 |
| agtctccatg | tttcttcatc | catctatcac | aaaaacacac | aaa | | 1183 |

<210> SEQ ID NO 5
<211> LENGTH: 891
<212> TYPE: DNA
<213> ORGANISM: artificial
<220> FEATURE:
<223> OTHER INFORMATION: Erwinia uredovora
<220> FEATURE:
<221> NAME/KEY: misc_feature
<222> LOCATION: (1)..(891)
<223> OTHER INFORMATION: crtB coding seqeunce

<400> SEQUENCE: 5

| | | | | | |
|---|---|---|---|---|---|
| atggctgttg | gctcgaaaag | ttttgcgact | gcctcaaagt | tatttgatgc | aaaaacccgg | 60 |
| cgcagcgtac | tgatgctcta | cgcctggtgc | cgccattgtg | acgatgttat | tgacgatcag | 120 |
| acgctgggct | tcaggcccg | gcagcctgcc | ttacaaacgc | ccgaacaacg | tctgatgcaa | 180 |
| cttgagatga | aaacgcgcca | ggcctatgca | ggatcgcaga | tgcacgaacc | ggcgtttgcg | 240 |
| gcttttcagg | aagtggctat | ggctcatgat | atcgccccgg | cttacgcgtt | tgatcatctg | 300 |
| gaaggcttcg | ccatggatgt | acgcgaagcg | caatacagcc | aactggatga | tacgctgcgc | 360 |
| tattgctatc | acgttgcagg | cgttgtcggc | ttgatgatgg | cgcaaatcat | gggcgtgcgg | 420 |
| gataacgcca | cgctggaccg | cgcctgtgac | cttgggctgg | catttcagtt | gaccaatatt | 480 |
| gctcgcgata | ttgtggacga | tgcgcatgcg | ggccgctgtt | atctgccggc | aagctggctg | 540 |

```
gagcatgaag gtctgaacaa agagaattat gcggcacctg aaaaccgtca ggcgctgagc    600
cgtatcgccc gtcgtttggt gcaggaagca gaaccttact atttgtctgc cacagccggc    660
ctggcagggt tgcccctgcg ttccgcctgg gcaatcgcta cggcgaagca ggtttaccgg    720
aaaataggtg tcaaagttga acaggccggt cagcaagcct gggatcagcg gcagtcaacg    780
accacgcccg aaaaattaac gctgctgctg gccgcctctg gtcaggccct tacttcccgg    840
atgcgggctc atcctccccg ccctgcccat ctctggcagc gcccgattta g             891
```

<210> SEQ ID NO 6
<211> LENGTH: 210
<212> TYPE: DNA
<213> ORGANISM: artificial
<220> FEATURE:
<223> OTHER INFORMATION: Pisum sp
<220> FEATURE:
<221> NAME/KEY: misc_feature
<222> LOCATION: (1)..(210)
<223> OTHER INFORMATION: DNA sequence coding for tps leader transit
      peptide

<400> SEQUENCE: 6

```
atggcttcta tgatatcctc ttccgctgtg acaacagtca gccgtgcctc taggggggcaa     60 tccgccgcag tggctccatt cggcggcctc aaatccatga ctggattccc agtgaagaag    120
gtcaacactg acattacttc cattacaagc aatggtggaa gagtaaagtg catgaacaac    180
ccttctcttc ttaaccatgc tgttgagacc                                      210
```

<210> SEQ ID NO 7
<211> LENGTH: 1927
<212> TYPE: DNA
<213> ORGANISM: artificial
<220> FEATURE:
<223> OTHER INFORMATION: Vinga mungo
<220> FEATURE:
<221> NAME/KEY: misc_feature
<222> LOCATION: (1)..(1927)
<223> OTHER INFORMATION: SH-EP promoter
<220> FEATURE:
<221> NAME/KEY: misc_feature
<222> LOCATION: (1674)..(1927)
<223> OTHER INFORMATION: nos polyadenylation site

<400> SEQUENCE: 7

```
gagcttaact tttgaggcag agcttgtaaa ttgtaacagg tgaggtagaa agacggaaag     60
tacttttaat aataaaaggt ttgaaaaatt aagaaaagaa gaagaaaata ttttgtgagt    120
gcacgcgatg gatctaatcc ttccatgaaa aagaatatca agaataacaa aaattgacaa    180
aatcagcgaa tacttcaccc aaaagtctac acaataataa atgctaaatc acatataatt    240
tgtgatgcat aacgcattac gctatcgtaa tcctttacaa caagcaagaa cgtcatccca    300
gaatctcaac tcaaatcaaa accgttcatt cataaataaa aatattctt acattctttt     360 gcaaatagaa cctttgccaa attgaaataa caaactctag gtatttgtca aattaactta    420
ccaacttctc gttatataat tttagattta taatcatgtc tataaattat ttctatacac    480
tctctctcaa atttgacctt tacattctgt gatttatttg aacagaataa atcactgtaa    540
aactaaacaa ctctttaaaa aaggtaaatt aggaaaagtc gaaatcaata aattataaat    600
caatccctag aaaactgcaa gataatattc ttaccaaaat catttaaata aatttgtaag    660
ttttttcttt ataccaattt tctgagaccc agagacattc ttaaattcat aacaacggtt    720
ttaagtatca gagtataaca tctttgtata aatagatttt tgaacgttca ataactaaca    780
```

-continued

```
cgtcagtttt tgtttccacg ttgtacgttt aataacaata aatgcgtgag ttagattact     840
aatcagaagt tagaagtgta caagactaac tttatacaga aatatattgt ttcagactgc     900
actttatggt gcgtagcacc tcaaaactct tacctttcgc atacattttc acacttcatc     960
caaacctttc gaaaagtcac ttcccttata ttaaaggact atgatataaa aaagactata    1020
tgtgttacta atttattggt ttgtatattt gtaataaatc gttccatcaa gaggagctat    1080
cacatattga gaacagtaaa aaaaaaaaaa agttggtaaa aaaacatttt cttatattat    1140
atcataaaat cagttaccat agtattttag agttttcaga ataatgcttc acccaacttg    1200
caactcattg tgcctcaaaa caggacgtaa ccatgttact cactctcctg cacaacccct    1260
tgttaaactg atagcgtgat cagcatgcaa gagaaagatg attcttgaag catacgataa    1320
cagattgaat gtgacaaaaa gtttgtgtct cagcttcagg gtcggcacct aatcaaaag     1380 gaaaatttgt caggtttcct tccgtagttt cattcactat tattgaatcc tttggctacc    1440
attcttgaga aacacaaaca cttcttatat ctgttctaca caattctctg agtgcgtgcc    1500
acagtttggt atcttcatga ttgctcattg ttcatgccca taaggaacat gtaacttcct    1560
catttattta ttattgcttt tgttttcttc tcactagtta actttcgttt ccctatataa    1620
accctccttt gttcccttcc cttcccatct tccatttatt gattccaaac acaatcgttc    1680
aaacatttgg caataaagtt tcttaagatt gaatcctgtt gccggtcttg cgatgattat    1740
catataattt ctgttgaatt acgttaagca tgtaataatt aacatgtaat gcatgacgtt    1800
atttatgaga tgggttttta tgattagagt cccgcaatta tacatttaat acgcgataga    1860
aaacaaaata tagcgcgcaa actaggataa attatcgcgc gcggtgtcat ctatgttact    1920
agatcga                                                              1927
```

<210> SEQ ID NO 8
<211> LENGTH: 7
<212> TYPE: DNA
<213> ORGANISM: artificial
<220> FEATURE:
<223> OTHER INFORMATION: TATA-box

<400> SEQUENCE: 8 tatataa        7

<210> SEQ ID NO 9
<211> LENGTH: 1659
<212> TYPE: DNA
<213> ORGANISM: artificial
<220> FEATURE:
<223> OTHER INFORMATION: Vinga mungo
<220> FEATURE:
<221> NAME/KEY: misc_feature
<222> LOCATION: (1)..(1656)
<223> OTHER INFORMATION: changed SHEP promoter with three tet-operators
      in the vicinity of the TATA box
<220> FEATURE:
<221> NAME/KEY: misc_feature
<222> LOCATION: (1591)..(1609)
<223> OTHER INFORMATION: Tet operator
<220> FEATURE:
<221> NAME/KEY: misc_feature
<222> LOCATION: (1611)..(1617)
<223> OTHER INFORMATION: TATA-box
<220> FEATURE:
<221> NAME/KEY: misc_feature
<222> LOCATION: (1620)..(1638)
<223> OTHER INFORMATION: Tet operator
<220> FEATURE:
<221> NAME/KEY: misc_feature
<222> LOCATION: (1641)..(1659)

<223> OTHER INFORMATION: Tet operator

<400> SEQUENCE: 9

```
cttaactttt gaggcagagc ttgtaaattg taacaggtga ggtagaaaga cggaaagtac        60
ttttaataat aaaaggtttg aaaaattaag aaaagaagaa gaaatatttt tgtgagtgca       120
cgcgatggat ctaatccttc catgaaaaag aatatcaaga ataacaaaaa ttgacaaaat       180
cagcgaatac ttcacccaaa agtctacaca ataataaatg ctaaatcaca tataatttgt       240
gatgcataac gcattacgct atcgtaatcc tttacaacaa gcaagaacgt catcccagaa       300
tctcaactca aatcaaaacc gttcattcat aaataaaaaa tattcttaca ttcttttgca       360
aatagaacct tgccaaatt gaaataacaa actctaggta tttgtcaaat taacttacca       420
acttctcgtt ataatttt agattataa tcatgtctat aaattatttc tatacactct       480
ctctcaaatt tgacctttac attctgtgat ttatttgaac agaataaatc actgtaaaac       540
taaacaactc tttaaaaaag gtaaattagg aaaagtcgaa atcaataaat tataaatcaa       600
tccctagaaa actgcaagat aatattctta ccaaaatcat ttaaataaat ttgtaagttt       660
tttctttata ccaattttct gagacccaga gacattctta aattcataac aacggtttta       720
agtatcagag tataacatct ttgtataaat agatttttga acgttcaata actaacacgt       780
cagttttgt ttccacgttg tacgtttaat aacaataaat gcgtgagtta gattactaat       840
cagaagttag aagtgtacaa gactaacttt atacagaaat atattgtttc agactgcact       900
ttatggtgcg tagcacctca aaactcttac ctttcgcata cattttcaca cttcatccaa       960
acctttcgaa aagtcacttc ccttatatta aaggactatg atataaaaaa gactatatgt      1020
gttactaatt tattggtttg tatatttgta ataaatcgtt ccatcaagag gagctatcac      1080
atattgagaa cagtaaaaaa aaaaaaaagt tggtaaaaaa acattttctt atattatatc      1140
ataaaatcag ttaccatagt atttagagt tttcagaata atgcttcacc caacttgcaa      1200
ctcattgtgc ctcaaaacag gacgtaacca tgttactcac tctcctgcac aaccccttgt      1260
taaactgata gcgtgatcag catgcaagag aaagatgatt cttgaagcat acgataacag      1320
attgaatgtg acaaaaagtt tgtgtctcag cttcagggtc ggcacctaat acaaaaggaa      1380
aatttgtcag gtttccttcc gtagtttcat tcactattat tgaatccttt ggctaccatt      1440
cttgagaaac acaaacactt cttatatctg ttctacacaa ttctctgagt gcgtgccaca      1500
gtttggtatc ttcatgattg ctcattgttc atgcccataa ggaacatgta acttcctcat      1560
ttatttatta ttgcttttgt tttcttctca actctatcac tgatagagtc tatataaaca      1620
ctctatcact gatagagtga actctatcac tgatagagt                             1659
```

<210> SEQ ID NO 10
<211> LENGTH: 1293
<212> TYPE: DNA
<213> ORGANISM: artificial
<220> FEATURE:
<223> OTHER INFORMATION: Brassica napus
<220> FEATURE:
<221> NAME/KEY: misc_feature
<222> LOCATION: (1)..(1239)
<223> OTHER INFORMATION: Changed CRU promoter with three tet operators
      in the vicinity of TATA box
<220> FEATURE:
<221> NAME/KEY: misc_feature
<222> LOCATION: (1226)..(1244)
<223> OTHER INFORMATION: Tet operator
<220> FEATURE:
<221> NAME/KEY: misc_feature
<222> LOCATION: (1246)..(1252)

```
<223> OTHER INFORMATION: Tata-box
<220> FEATURE:
<221> NAME/KEY: misc_feature
<222> LOCATION: (1254)..(1272)
<223> OTHER INFORMATION: Tet operator
<220> FEATURE:
<221> NAME/KEY: misc_feature
<222> LOCATION: (1275)..(1293)
<223> OTHER INFORMATION: Tet operator

<400> SEQUENCE: 10
cttctacacg ttttgaaaag ttaacctgtt ggttaaatgg ttagctatga ctctcgcaac      60
aaacccaacc cttaagatga tgatggttta acatttgaca acatagttaa gactgtgtct     120
atataatagt caacaaattc agattgtagt attatggagt caacatattt cgagatcaaa     180
aacattcaaa acgtaaatct atcgacgtct cacatagttt tgttatgaag ctgatgaaaa     240
aagttggaag acatagtttt gcaaacatca tttgttgcta acgtataaac gttggtttga     300
ttaaatgtaa taggataagg atatccgttt gttcatataa ttgagttaaa ttatattttg     360
gttattataa tatgttaagt tgaaaataaa taggtccaac aaccttgttt aaatagattt     420
tttaggagtg attccctttt aatagtatag attatactct cttcctaatc gaccttccgt     480
ggggtaaagt ggtcaattat attctttatg gatgagcttg attgagaatg ggtttatggg     540
ttatgacaag ggcatgtaca aatgtcactg cctcttgaca tgcaaccgaa cagttggcga     600
ctcaagtcgc agaagataca acggaccaaa ccctccgagt gtcgccgcgt ctgttatgtg     660
tcaccttttt gtctccttt cttaaaaatt ggtaactcat tttcaaaaa agaagagga     720 tagttttggc tgtatctcct aaactattcg atcacaacgc cagatatttt aatactggat     780
actagtgatg taatttgatt tgttaattgt caaaaagtag attctcctat ctcgttttta     840
gttcaattat tatatggtta aatgaattta agtcgattag aaatgattag ttaatcaacc     900
agagttgctc tataagtcta tactgataac atgaaccatt ttctaaaaat gagatagata     960
catttgaatt ttgtcgtggt ttggagtatg cggagatagt cgtacgcgca tgaacatcat    1020
gagacacttg cttcagctca cagagtgacg tgtaaagacc atagacccac gacttcatgc    1080
aaacccattc ctacgtggca caaaccttca tgctcactcc acatatataa actcctacca    1140
agtctccatg tttcttcatc catctatcac aaaaacacac aaatagaccc acgacttcat    1200
gcaaacccat tcctacgtgg cacaaactct atcactgata gagtctatat aagactctat    1260
cactgataga gtgaactcta tcactgatag agt                                 1293

<210> SEQ ID NO 11
<211> LENGTH: 19
<212> TYPE: DNA
<213> ORGANISM: artificial
<220> FEATURE:
<223> OTHER INFORMATION: Tet operator

<400> SEQUENCE: 11
actctatcac tgatagagt                                                   19

<210> SEQ ID NO 12
<211> LENGTH: 18
<212> TYPE: DNA
<213> ORGANISM: artificial
<220> FEATURE:
<223> OTHER INFORMATION: Bacillus amyloliquefaciens
<220> FEATURE:
<221> NAME/KEY: misc_feature
<222> LOCATION: (1)..(18)
<223> OTHER INFORMATION: Primer for SHEPp barnase1 pAnos
```

<220> FEATURE:
<221> NAME/KEY: misc_feature
<222> LOCATION: (1)..(18)
<223> OTHER INFORMATION: SHEPp5;UTR-5'CDS barnase 1 primer

<400> SEQUENCE: 12
acacaaccat ggcacaag                                               18

<210> SEQ ID NO 13
<211> LENGTH: 18
<212> TYPE: DNA
<213> ORGANISM: artificial
<220> FEATURE:
<223> OTHER INFORMATION: Bacillus amyloliquefaciens
<220> FEATURE:
<221> NAME/KEY: misc_feature
<223> OTHER INFORMATION: 3;UTR-pAnos-Reverse primer
<220> FEATURE:
<221> NAME/KEY: misc_feature
<223> OTHER INFORMATION: 3'UTR-pAnos-Reverse primer

<400> SEQUENCE: 13
gagctcgagg gcgcgtct                                               18

<210> SEQ ID NO 14
<211> LENGTH: 17
<212> TYPE: DNA
<213> ORGANISM: artificial
<220> FEATURE:
<223> OTHER INFORMATION: Bacillus amyloliquefaciens
<220> FEATURE:
<221> NAME/KEY: misc_feature
<223> OTHER INFORMATION: CRUp5'UTR-5'CDSbarnase1 primer

<400> SEQUENCE: 14
cacacaaaca ccatggc                                                17

<210> SEQ ID NO 15
<211> LENGTH: 30
<212> TYPE: DNA
<213> ORGANISM: artificial
<220> FEATURE:
<223> OTHER INFORMATION: Bacillus amyloloquefaciens
<220> FEATURE:
<221> NAME/KEY: misc_feature
<223> OTHER INFORMATION: 3'UTR-p-A35S-Reverse primer
    CRUp-barnase1-pA35S
<220> FEATURE:
<221> NAME/KEY: misc_feature
<223> OTHER INFORMATION: 3'UTRpA35Sp Reverse primer

<400> SEQUENCE: 15
gatttgtaga gagagactgg tgatttttgc                                  30

<210> SEQ ID NO 16
<211> LENGTH: 624
<212> TYPE: DNA
<213> ORGANISM: artificial
<220> FEATURE:
<223> OTHER INFORMATION: E. coli transposon Tn10
<220> FEATURE:
<221> NAME/KEY: misc_feature
<223> OTHER INFORMATION: TetR gene

<400> SEQUENCE: 16
atgtccagat tagataaaag taaagtgatt aacagcgcat tagagctgct taatgaggtc    60
ggaatcgaag gtttaacaac ccgtaaactc gcccagaagc taggtgtaga gcagcctaca   120
ttgtattggc atgtaaaaaa taagcgggct ttgctcgacg ccttagccat tgagatgtta   180

```
gataggcacc atactcactt ttgcccttta gaaggggaaa gctggcaaga ttttttacgt      240
aataacgcta aaagttttag atgtgcttta ctaagtcatc gcgatggagc aaaagtacat      300
ttaggtacac ggcctacaga aaaacagtat gaaactctcg aaaatcaatt agccttttta      360
tgccaacaag gtttttcact agagaatgca ttatatgcac tcagcgctgt ggggcatttt      420
actttaggtt gcgtattgga agatcaagag catcaagtcg ctaaagaaga aagggaaaca      480
cctactactg atagtatgcc gccattatta cgacaagcta tcgaattatt tgatcaccaa      540
ggtgcagagc cagccttctt attcggcctt gaattgatca tatgcggatt agaaaaacaa      600
cttaaatgtg aaagtgggtc ttaa                                              624
```

DOUBLE RECOVERABLE BLOCK OF FUNCTION

This application is a Continuation-in-Part of application Ser. No. 09/617,543, filed on Jul. 14, 2000, now U.S. Pat. No. 6,849,776, which is incorporated herein by reference.

SEQUENCE DATA

This application contains sequence data provided on a computer readable diskette and as a paper version. The paper version of the sequence data is identical to the data provided on the diskette.

TECHINCAL FIELD

This invention relates, in general, to containment of plant germplasm and, in particular to a method and a DNA construct for controlling segregration of transgenes in plants.

BACKGROUND

The techniques of plant biotechnology have improved during the last ten years so that most of the crop species that are important to the mankind can be routinely transformed. The industry seeks for new traits not only for agricultural or nutritional purposes but as well for pharmaceutical purposes. There is an increasing interest to develop efficient and economic production systems for useful biological compounds. Transgenic plants are in the scope of research aiming to develop such a system. Given the concerns of environmental impacts of genetically modified crops this development has clearly created a need for a reliable system to prevent transgene flow among crops and in their relatives. Accordingly, several research groups around the world are currently engaged in developing techniques for gene containment in transgenic crops. The present invention discloses an improved transgene containment method and tools to achieve transgene containment. The method according to the present disclosure is superior in its reliability as compared to the systems that are known in the prior art.

Basically, the technologies that are aimed to prevent transgene flow can be categorized into one-component and two-component technologies. The main feature of the one-component systems is a possession of factor for negative selection of transgene from plant population. As an example there are well known concepts of male sterility, chloroplast transformation or 'Terminator' technology. The one-component systems are capable of decreasing gene flow but they do not provide an absolutely reliable containment. Therefore, one component systems might not give the wished result in situations where a total prevention of transgene flow is wanted.

The two-factor technologies are recently developed for improved transgene containment. Generally these systems use negative selection factors together with recovering (rescuing or repairing) factor. The negative selection factors are usually lethal for the plant and therefore they can absolutely prevent the transgene flow. The rescuing factor represses the action of the selection factor, disrupts its function or recovers the functions it blocked. Examples of two factor technologies are systems described in international patent publications WO 94/03619 (Bright et al.) and WO 00/37660 (Fabijanski et al).

International patent publication WO 02/064801 (Kuvshinov et al) describes a two-factor system, where excision construct (EC) is linked to the TGI. The EC excises the whole insert from the genome of the host organism under natural conditions. Artificially activated repression construct represses the action of the EC and saves the transgenic insert in the host genome. This system removes the entire transgene insert and leaves the host genome free from the foreign genes. Thus, in natural conditions transgenic plant produces non-transgenic seeds only and can not produce transgenic seeds.

Although the publications described above give advanced alternatives to control transgene flow, none of them resolves the problem of the negative selection gene being inactivated by mutagenesis or by silencing mechanism. According to Gressel (1999), such an inactivation of negative selection factor (gene) can happen approximately with a frequency of $10^{-6}$. In practice this means once in each middle sized field plot during a growth season. Such a frequency of gene escape for example from a field where the transgenic crop is cultivated for production of a vaccine or other pharmaceutical compound would create concerns of various parties.

This problem of inactivation has been proposed to be solved by one-component concept called mitigation tandem technique. In this technique the desired transgene is coupled in tandem with gene(s) that would render hybrid offspring or volunteer weeds less able to compete with crops, weeds and wild species. Examples of features that could be used in mitigation technique are secondary dormancy and dwarfing. The problem encountered with the tandem mitigation technique is that due to absence of a recovering system removal of transgene from the population demands several generations and therefore this technique does not provide a system reliable enough for transgene containment. Another limitation of the technology is scarce sources of genes capable to mitigation.

U.S. patent application Ser. No. 09/617,543 (Kuvshinov et al.), now U.S. Pat. No. 6,849,776 discloses a two-factor system called RBF (recoverable block of function system) comprising at least one bClocking construct (BC) linked to a transgene of interest TGI and a recovering construct (RC). According to this disclosure BC blocks a vital physiological or molecular function of the host plant through developmental or organ specific expression. The RC is induced by an externally controllable stimulus and when induced it recovers the function previously blocked by expression of the BC(s). The present disclosure describes an improved RBF system.

The improved RBF system according to the present disclosure markedly decreases the probability of breach of the gene containment due to mutagenesis or silencing of the selection factor (i.e. the blocking sequence of the BC). The invention according to the present disclosure contains two blocking constructs. According to the present invention blocking nucleotides in the two blocking constructs may be different whereby the breach of the containment system becomes clearly less probable than in any of the previously described systems. The system includes a recovering mechanism whereby the progeny can carry the transgene of interest only under controlled recovery process.

SUMMARY OF INVENTION

An object of the present invention is to provide a reliable method for molecular control of gene containment in sexually reproducing transgenic plants. The increased reliability of the present invention is due to minimizing effects of silencing and crossing overs in the recoverable block of function into which the method is based.

The method is achieved by providing a plant with a recoverable block of function (RBF) system which comprises two blocking constructs (BC) and a transgene of interest (TGI) encoding desired gene products. The TGI is placed in between the two BCs. Both of the BCs comprise a blocking gene that is capable of blocking at least one molecular or physiological function essential for development or reproduction of the plant. Importantly the blocking genes may code for the same protein or they may code for different proteins. When coding for the same protein the nucleotide sequence of the blocking genes may still be different from each other. The blocking genes are driven by development/organ specific promoters, which may be similar or different. The RBF system also comprises a recovery system which may comprise at least one recovering construct (RC) activatable by an externally applicable and controllable intervention step. Activation of the RC leads to recovery of the functions blocked by the BCs and thereby the development or reproduction of the plant is rescued. According to the present disclosure recovery of blocked functions may also be obtained merely with an external intervention without an RC.

A further object of the present invention is to provide a molecular control of gene containment that can be provided in one insert or in two inserts. In a one insert system the RC/RCs are locating in the same insert and thereby in same chromosome as the BCs and the TGI. In a two insert system the RC/RCs are locating in separate insert and thereby in different chromosomes than the BCs and the TGI.

An even further object of the present invention is to provide a molecular control of gene containment where the RC/RCs are recoverable by physical or chemical treatment or by support of homozygous conditions, whereby constitutively expressing RC and the BC are not segregated.

Still another object of the present invention is to provide a molecular control of gene containment where the recovery mechanism is completed by an external intervention without an RC.

Also contemplated in the present invention are kits comprising instructions for cloning vectors with or without selected TGI, wherein the cloning vectors without TGI have a place for inserting the desired TGI, as well as cells or cell-lines for convenient preparation of transgenic plants harboring one or more DNA construct complexes providing the gene containment according to the present invention.

The characteristic features of the present invention are defined in more detail in the claims.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A T-region of pVK31 plant transformation vector contains two BCs encoding the same barnase mRNA driven by different promoters (SH-EPp and CRUp). The BCs flank GUS gene from the both sides.

FIG. 1B Recovering construct (RC) is in a separate insert. Barstar gene is under heat shock or 35S promoter cloned in the T-region of plant transformation vector.

FIG. 5 depicts alignment of two barnase genes. Untranslated regions (UTR) and coding sequences of two barnase genes used in BCs of pVK34 vector are aligned to show their similarity. Similarity between GC-enriched barnase1 and AT-enriched barnase 2 in the coding region (gray boxes) reached 80%. Similarity between the mRNA of the barnases including UTRs is under 70%. Upper row presents barnase1 sequence and lower level barnase2 sequence. Start and end of transcription are marked as well as 5' and 3' UTRs.

FIG. 6A over expression or unspecific expression of BCs resulted in abnormal phenotype with dwarfish plants, swirled leaves and undeveloped inflorescence.

FIG. 6B Plants expressing BCs normally revealed normal vegetation and phenotype. However, after flowering the flowers with ovary dried without further formation of fruit because of expression of barnase driven by CRU promoter.

FIG. 6C Transgenic plants shown in FIG. 6B produced normal fruits and viable seeds after heat shock treatment.

FIG. 7A Expression of barnase1 in tobacco embryos. 10 μg of embryo total RNA isolated from plants of pVK34 and pVK35 lines and unlabeled barnase1 control RNA mixed with 10 μg of non-transgenic carrier embryo total RNA were hybridized with barnase1 RNA probe. 10 μg of unlabeled barnase2 RNA was mixed with 10 μg of carrier RNA and loaded in lane 8. It demonstrated that background caused by cross-hybridization between barnase1 and barnase2 is less than 3%. Barnase signals in pVK35 lines carrying only barnase2 gene were close to background level. Double RBF lines carrying pVK34 expressed 0.01 to 0.05 pg barnase1 mRNA per 1 μg of total embryo RNA.

FIG. 7B Expression of barnase2 in tobacco embryos. The same preparations from transgenic tobacco embryos as in FIG. 7A were loaded in the gel and compared to 0-30 pg of synthesized cold barnase2 RNA. In pVK34 and pVK35 lines expression of barnase2 was close to 0.03 pg per μg.

FIG. 7C Expression of barstar in tobacco embryos. 5 μg samples of the same total RNA preparations were hybridized with barstar probe and compared with 0-20 pg of synthesized cold barstar RNA mixed with 5 μg carrier embryo RNA. Expression of barnase mRNA ranged from 0.04 to 1.0 pg per μg of total embryo RNA.

FIG. 9 depicts a one insert double RBF consisting of two BCs different in their structure and function.

FIG. 9A depicts a system with one RC. The construct contains GUS gene as the TGI, tetR gene under HSp as the RC, crtB (Phytoene synthase) gene under SH-EP promoter as the BC1 and barnase gene under CRU promoter as the BC2. Promoters of the BCs contain tet operator sequences (O).

FIG. 9B depicts a system with two RCs. The construct contains GUS gene as the TGI, tetR gene under HSp as the RC1, barstar gene under HSp as the RC2, crtB (Phytoene synthase) gene under SH-EP promoter containing tet operator sequence (O) as the BC1 and barnase gene under CRU promoter as the BC2.

FIG. 15 shows the results of germination assays of tobacco seeds carrying pVK31 HSp-barstar constructs. (Abbreviations: NTS— non transgenic tobacco *Nicotiana tabacum* cv. Samsung); HS-heat shock).

FIG. 16 shows the results of germination assays on tobacco seeds carrying pVK31+pGPTV-KAN-35Sp-barstar construct. (Abbreviations: NTS—non transgenic tobacco *Nicotiana tabacum* cv. Samsung).

Terms Used in the Disclosure

Figure 1:
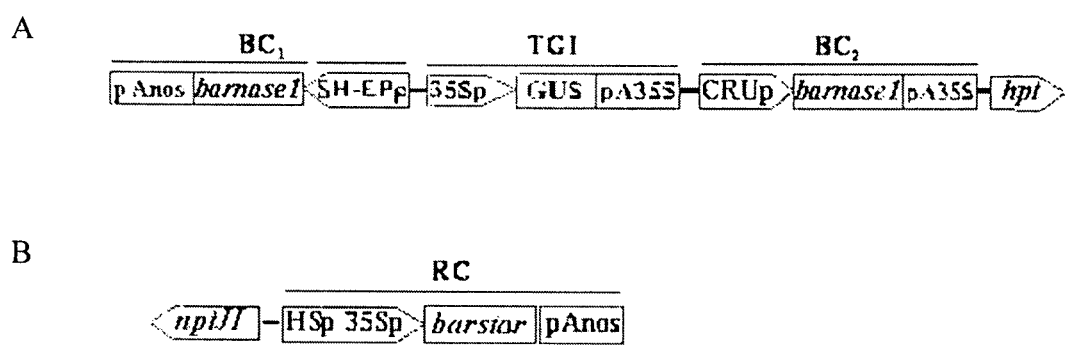
FIG. 1 depicts the DNA construct of segregating double RBF of Examples 2 and 3.

In the present disclosure most of the terms used have the same meaning as they generally have in the field of recombinant DNA techniques, molecular biology and in plant production related sciences. Some terms are however, used in a somewhat different way and are explained in more details below.

Segregating Recoverable Block of Function System is synonymous to Delayed Recoverable Block of Function system. Both of these terms describe an RBF system in which the RC is situated in a different non-allelic chromosome apart from the BCs and the TGI. Segregating RBF system is produced by using two-insert system described in Examples 1-4.

Simple Recoverable Block of Function System is a system without an RC construct. The recovery of blocked functions is obtained by external intervention only.

One-insert system is synonymous to Single-insert system. Both of these terms mean that all components of RBF are situated in the same DNA-insert and are integrated into one site of the plant genome/chromosome.

DETAILED DESCRIPTION OF THE PREFERRED EMBODIMENT

The present disclosure is related to methods of molecular biology for controlling transgene segregation and introgression into a population of sexually compatible plants. The present invention also discloses kits to be used in the method of the invention. The control of transgene segregation is achieved through a complex of DNA constructs herein called a double recoverable block of function (RBF) system. The double RBF system according to this disclosure comprises two blocking constructs (BC1 and BC2). Each of the blocking constructs consists of a nucleotide sequence capable of blocking a particular physiological or developmental function of the host plant. Therefore the expression of the nucleotide sequence of the blocking construct leads to such a change of the physiology and/or morphology of the plant that the plant is not anymore capable of reproduction. The blocking sequences of the two blocking constructs according to this disclosure may be similar to each other or they may be different from their sequence to an extent that they both still encode the same protein. It is also possible to choose the blocking sequences so that they encode different proteins.

The blocking genes in the BCs may be driven by similar or different promoters. Importantly the promoters are so chosen that the blocking genes are expressed in critical organs and/or at a critical time period as to prevent the reproduction. More specifically the promoters are so chosen that they express at selected specific development stages such as but not limited to seed germination, embryo development, stem elongation, and inflorescence.

Examples of suitable organ or developmental stage specific promoters are SH-EP promoter expressing during seed germination/embryo development and CRU-promoter expressing in embryos. Other suitable development stage specific promoters are e.g. LEA promoters expressing at late embryo development stages.

The system also comprises a transgene of interest (TGI), expression of which leads to production of desired compounds or characteristics of the transgenic plant. More than one TGI may also be used in the system. A kit according to the present invention may contain construct having the TGI already inserted therein but alternatively the kit may contain a construct having an empty place for TGI insertion. Examples of TGIs are isolated and purified genes or artificial genes, which have been constructed synthetically or semi synthetically from parts of isolated and purified genes, using different methods. The DNA sequences of said artificial or isolated and purified genes may encode useful pharmaceuticals or parts thereof, such as human serum albumin and its modifications, lysozyme, antibodies and their modifications, other beneficial peptides, proteins, such Cry proteins or any other desirable compound. TGI may as well be a gene that regulates some metabolic pathway thereby for example increasing or decreasing contents of some biochemical intermediates or leading to a modified phenotype. The object of the RBF system is to prevent the TGI from escaping into compatible plants. According to the present disclosure the desired TGI is to be placed in between of the two BCs. In the examples described below we use GUS-gene as a model-TGI. In the examples the TGI is placed under control of 35S promoter. For one skilled in the art it is clear that use of this TGI and promoter are not meant to limit the scope of the invention but described here merely as an example.

Furthermore, the RBF system according to this disclosure may comprise a recovering construct (RC). The RC comprises a nucleotide sequence that when expressed is capable of recovering the function blocked by the BCs. In a preferred embodiment the recovering nucleotide sequence is driven by a promoter that is inducible by an external intervention. The external intervention may be for example a physical or a chemical treatment that can be controlled by human being. Thereby, the transgenic plants carrying the RBF system according to this disclosure can be made reproductive by a controlled treatment by human being. Examples of suitable inducible promoters are heat shock inducible promoters. An example of chemically inducible promoters is among others maize glutatione-S-transferase gene promoter (GSTII-27) which is activated by herbicide Safeners R-25788 (WO 94/03619).

Figure 8:
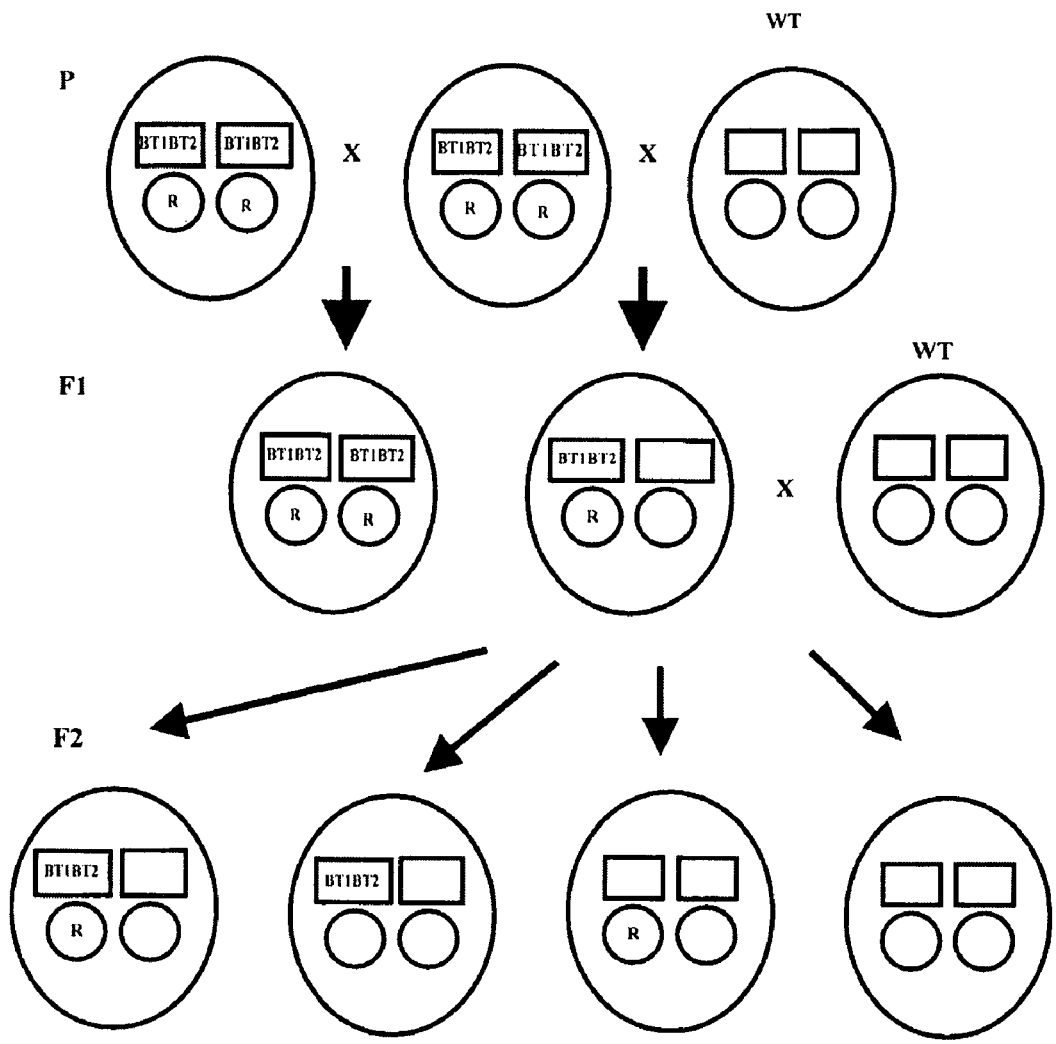
FIG. 8 Illustrates hybridization of segregating double RBF. Chromosomes carrying blocking constructs (B1 and B2) linked to the gene of interest (T) as well as recovering construct (R) placed in a different non-allelic chromosome are shown. Wild type (WT) chromosomes are shown without markings. The parental plants (P) included in hybridization are shown in the first line. The condition of genes involved in RBF does not change in result of intraline crossing. Intraline F1 progeny has the homozygous genotype for RBF and the gene of interest. External regulation of the RBF implies to support homozygous condition of the transgenes through intraline hybridization. In case of outside hybridization, the first F1 hybrid progeny genotypes are heterozygous for all transgene constructs. The plants remain alive. The segregating RBF starts to act from F2 hybrid progeny onward in case of outside hybridization. In F2 hybrids, only half of the plants carry blocking construct linked to the transgene of interest. Half of them will be unable to reproduce because of absence of recovering constructs. Therefore, beginning from the second outside hybrid progeny, 50% negative selection eliminates the transgene of interest from natural population.

In alternative embodiments the coding sequence of RC may also be under constitutive promoter and the external intervention in such a case is intraline hybridization as described in Example 4 and illustrated in FIG. 8. Examples of suitable constitutive promoters are 35Sp of CaMV, NOSp and OCSp of *Agrobacterium tumefaciens*.

In a still another alternative embodiment the RBF system does not include an RC, but the recovery is achieved with the external intervention alone. An example of this embodiment is described in Examples 9 and 10 and illustrated in FIGS. 11 and 12.

In one alternative embodiment the blocking sequences of the BCs encode different proteins. This embodiment may contain two different RCs to recover the functions blocked by the two different BCs. According to another embodiment the system with two different BCs can also have one RC. In this embodiment repressor binding sequences have been introduced into the promoters of the BCs. The recovering gene of RC according to this embodiment encodes repressor (protein) of the promoters of the BCs. The recovering gene is under inducible promoter. Therefore, after induction of the RC expression, the repressor will bind the BC's promoters and repress expression of both of the BCs. This embodiment is described in Example 7 and illustrated in FIG. 9.

According to one embodiment of the present disclosure the DNA constructs of the BC and RC comprise synthetic sequences of barnase and barstar genes, respectively. The barnase gene may be synthesized with different nucleotide content, e.g. enriched GC-content or with enriched AT-content. According to a specific embodiment of the present disclosure the synthetic barnase sequence is according to SEQ ID NO: 1 or SEQ ID NO: 2. According to one specific embodiment the synthetic barstar sequence is according to SEQ ID NO: 3.

According to other embodiments the blocking sequences of the BCs can be selected from the genes listed in Table 1 below.

TABLE 1

According to alternative embodiments of the present disclosure the blocking sequences of the BCs may be selected from the genes listed here. The genes here listed here are examples of alternative embodiments and not meant to limit the scope of the invention. The two BCs may have same or different blocking sequence.

| Type of action | Examples | Reference |
| --- | --- | --- |
| DNA recombination | Cre, FTP-chromosome crossing | Stuurman et al. 1996 Plant Mol Biol 32: 901-913 |
| RNA silencing | Rubisco | Rodermel et al. 1988 Cell 55:673-681 |
| Phytotoxins/lethal genes | NPK15 | Ito et al. 1994 Mol Gen Genet 245:1-10 |
| Hormones | Aux1 + Aux2 | Fabijanski & Arnison WO 00/37660; Schernthaner et al PNAS 100 (2003) 6855-9 |
| Overproduction of metabolite or change of biosynthetic pathway | Phytoene synthase-overproduction of phytoene | |

The blocking nucleotide sequences of the BCs may be driven by various promoters. According to a preferred embodiment the promoters are organ or development stage specific. The developmental stages for temporal expression may be for example seed germination, flowering, embryo or fruit maturation, inflorescence formation, stem or root elongation.

According to one specific example the organ/development stage specific promoter is cruciferin promoter (CRUp) cloned from oil seed rape (*Brassica napus*). Cruciferin is the second most abundant storage protein of oilseed rape seeds. Its expression is embryo specific.

According to another specific embodiment the promoter driving blocking nucleotide sequences is SH-EP promoter cloned from *Vinga mungo*. Originally SH-EP-cysteine endopeptidase (Yamauchi et al., 1996, Plant Mol. Biol. 30: 321-329) expresses exclusively in the germinating seedlings of *Vinga mungo*. Expression starts on the second day after germination. The peak of the expression in germinating seeds occurs on the third day at the mRNA level and on the forth day on protein level. Enzymatic activity continues until 5th-6th day and then fades.

According to still another alternative embodiment the blocking nucleotides can be driven by LEA promoters expressing at late embryo development stages (Hughes and Galau, 1989; Galau, et al., 1992, Plant Physiol. 99: 783-788; Devic, et al., 1996, Plant J. 9: 205-2015). LEA promoters are highly specific to late embryogenesis and consequently applicable for driving BCs.

The promoter of the gene encoding for caffeic acid O-methyltransferase (COMT) enzyme expresses the protein highly specifically in the stem tissue of a perennial ryegrass *Lolium* perenne (McAlister, et al., 1998, Australian J. Plant Physiol. 25: 225-235). According to one alternative embodiment of the present disclosure this promoter is used to drive the blocking sequences to block inflorescence stem development.

A 620 bp promoter fragment from MT 1-A (metallothionein-like) gene is sufficient to direct expression in transformed cotton roots (Hudspeth, et al., 1996, Plant Mol. Biol. 31: 701-705). According to one alternative embodiment of the present disclosure this promoter is used to drive the blocking sequences to block root increase.

According to one embodiment Leafy cotyledon (LEC) genes are used as a source for the promoters driving the BC. LEC genes are central embryonic regulators that serve critical roles both at early and late embryo development. LEC1 gene of *Arabidobsis* is required for the specification of cotyledon identity and the completion of embryo maturation (Lotan et al. 1998 *Arabidopsis* Leafy cotyledon1 is sufficient to induce embryo development in vegetative cells. Cell, 93(7): 1195-205). LEC2 is required for the maintenance of suspensor morphology, specification of cotyledon identity, progression through the maturation phase, and suppression of premature germination (Stone et al. 2001 Leafy cotyledon2 encodes a B3 domain transcription factor that induces embryo development. PNAS 98(20):11806-11).

The promoter driving the recovering sequences in the RC may be inducible by an outside stimulus. Such a stimulus may be chemical or physical. Chemical stimulus can be any molecule capable of regulating the activity of a particular promoter. Physical stimulus can be for example temperature, osmosis, light, or gravitation.

According to one embodiment the promoter driving the recovering sequences in the RC may be a physically inducible promoter, such as a heat shock inducible promoter.

According to one specific embodiment a heat shock promoter is cloned from *Glycine max*.

According to one embodiment the recovering sequences in the RC may be driven by a promoter inducible by a chemical. An example of such a promoter is maize glutatione-S-transferase gene promoter (GSTII-27) which is activated by herbicide Safeners R-25788(WO 94/03619).

According to an alternative embodiment the promoter driving the RC may be constitutively expressing promoter, such as but not limited to 35S promoter.

According to still another embodiments the recovering method may include compensation of metabolite deficiency caused by BC action (Shown and described, in Examples 9 and 10); repression of promoter of BC as shown and described in Examples 7 and 8; silencing of BC mRNA by antisense RNA, enzymatic digestion or inactivation of metabolite product of BC by phosphate transferases for example; and compensation of overproduction of hormone or metabolite production.

The present disclosure is also related to kits to be used in the method according to the present disclosure to obtain contained use of transgenes. The kits preferably comprise a cloning vector having two BCs and one or more TGIs or a place for insertion of the TGIs in between of the two BCs. The cloning vector may further comprise one or more RCs. The kits preferably also comprise instructions for using the cloning vectors and applying the means for recovery with or without RCs.

The following examples are set forth to illustrate the method and tools and in no way to limit the scope of the invention.

EXAMPLE 1

DNA Cloning, Construct Design and Similarity of the Two Synthetic Barnase Genes Barnase and barstar genes originating from *Bacillus amyloliquefaciens* were used for design of synthetic genes with enriched GC or AT content. The genes were synthesized from 55-59 base long oligonucleotides in high fidelity polymerase chain reaction (PCR). Two synthetic barnase sequences were cloned: one with enriched GC content (SEQ ID NO: 1) and the other with enriched AT content (SEQ ID NO: 2). The genes are called barnase1 and barnase2, respectively. Similarity of the CDS (coding sequence) sequence of barnase1 and barnase2 in the coding region reached 80% as is shown in FIG. 5. Similarity between the mRNA sequences of barnase1 and barnase2 remained under 70%.

Maximum difference between coding sequences, which can be achieved by codon optimization, is about 35-40%. It would be clear to one skilled in the art that the present invention is not limited to SEQ ID NO: 1 and SEQ ID NO: 2, but any other modified barnase sequences can be used as well.

Heat shock promoter (HSp) of *Glycine max*, cysteine endopeptidase promoter (SH-EPp) of *Vigna mungo* and cruciferin promoter (CRUp) from *Brassica napus* were cloned using a high fidelity PCR. GUS (uidA) gene containing an intron sequence at the beginning of coding sequence was placed under the control of the 35S promoter and was used in the constructs as an example of transgene of interest (TGI).

Figure 2:
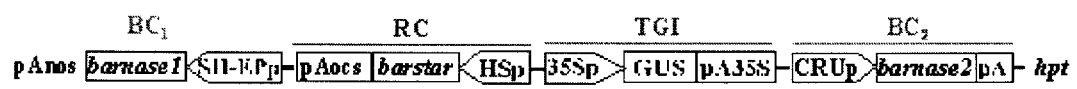
FIG. 2 depicts the double RBF in one insert as described in Example 4: T-region of pVK34 plant transformation vector has no repeated DNA sequences: BCs encode different barnases (GC enriched barnase 1 in BC1 and TA enriched barnase 2 in BC2, respectively) coding sequences cloned under different promoters and polyadenylation sites. TGI (GUS gene) and RC(HSp-barstar) are placed between the BCs.
Figure 4:
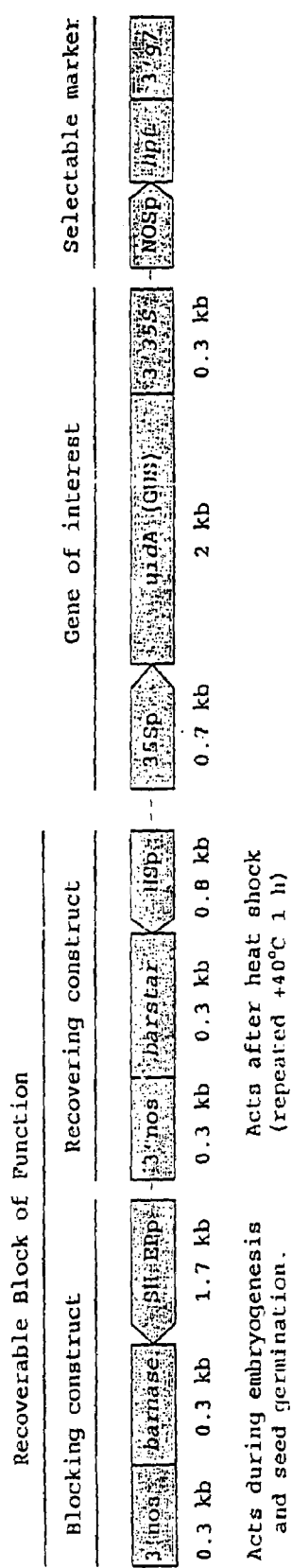
FIG. 4 depicts pVK18 plant transformation vector carrying single RBF consisting SH-EPp-barnase+35Sp-GUS+HSp-barstar. (The pVK18 vector served as basis for construction of pVK31 and pVK34 vectors of FIGS. 2 and 3).

Constructs for One Insert System Having Two BCs with Different Barnase Sequences (Barnase1 and Barnase1) and an RC (Barstar) Being Placed in Same Insert According to one embodiment the BCs and the RC are placed in the same insert. This one-insert system was developed using two different barnases (GC-enriched and AT-enriched barnase; barnase1 and barnase2, respectively). The sequences of the barnase genes (SEQ ID NO: 1 and SEQ ID NO: 2) are shown in FIG. 5. The pVK34 vector was developed from pVK18 vector depicted in FIG. 4 by inserting the second BC between GUS (TGI) and hpt (selectable marker) genes as shown in FIG. 2. In this example the BCs flank TGI and RC. BC2 consists of barnase2, which is regulated by CRU promoter ending with short artificial polyadenylation site (SEQ ID NO: 4). BC1 consists of barnase1 regulated by SH-EP promoter ending with nos polyadenylation site (SEQ ID NO: 7). Therefore, one-insert RBF construct according to this example has two BCs, which consists of different DNA and RNA sequences but encode still the same Barnase protein.

Constructs for Segregating System Having Two GC-Enriched Barnase Genes (Barnase1) Under Different Promoters and an RC (Barstar) in Another (Separate) Insert According to an alternative embodiment the BCs and the RC are located in different inserts and the RBF system according to this embodiment is a segregating double RBF. For a segregating system two inserts as shown in FIGS. 1A and 1B were constructed. The first insert containing RC (barstar under heat shock promoter or under 35S promoter) was cloned in pGPTV-KAN vector. The second transformation vector pVK31 contained two BCs (BC1 and BC2), both with the same GC-enriched barnase (barnase1) (SEQ ID NO: 1). In BC1 barnase1 was cloned under SH-EPp and in BC2 barnase1 was cloned under CRUp as shown in FIG. 1A. Thus both of the BCs expressed barnase mRNA having the same coding sequence. The pVK31 vector (FIG. 1A) was developed from pVK18 vector shown in FIG. 4 by removal of RC and placing BC2.

EXAMPLE 2

Transgenic Plants Having Segregating Double RBF System, in Which TGI (GUS) is Flanked by Two BCs Consisting the Same Barnase 1 Gene Under Different (SH-EPp and CRUp) Promoters and a RC in Another Insert Consisting of Barstar Gene Under Heat Shock Inducible Promoter.

Tobacco plants (*Nicotiana tabacum* cv. Samsung) were transformed by *Agrobacterium tumefaciens* strain LB4404 carrying pGPTV-KAN vector having the RC, which in this example was a barstar coding sequence (SEQ ID NO:3) driven by a heat shock promoter. Putative transformants were selected on 75 mg/l kanamycin. Transgenic plants were subjected to heat shock treatment and those plants that were positive in Northern analysis against barstar probe were chosen for second transformation with pVK31 (pGPTV-HPT/pBIN19-based) vector carrying the TGI (GUS in this example). Putative transformants were selected on 60 mg/l hygromycin. The TGI was placed in between of two BCs expressing the same coding sequence of barnase under different promoters as shown in FIG. 1A. Tobacco shoots that recovered on hygromycin selection were analyzed in histological GUS assay. GUS-positive plants were transferred from in vitro culture to the greenhouse for further studies.

Germination Tests

Figure 6:
FIG. 6 shows phenotypes of transgenic tobacco plants carrying pVK34 construct.
Figure 6:
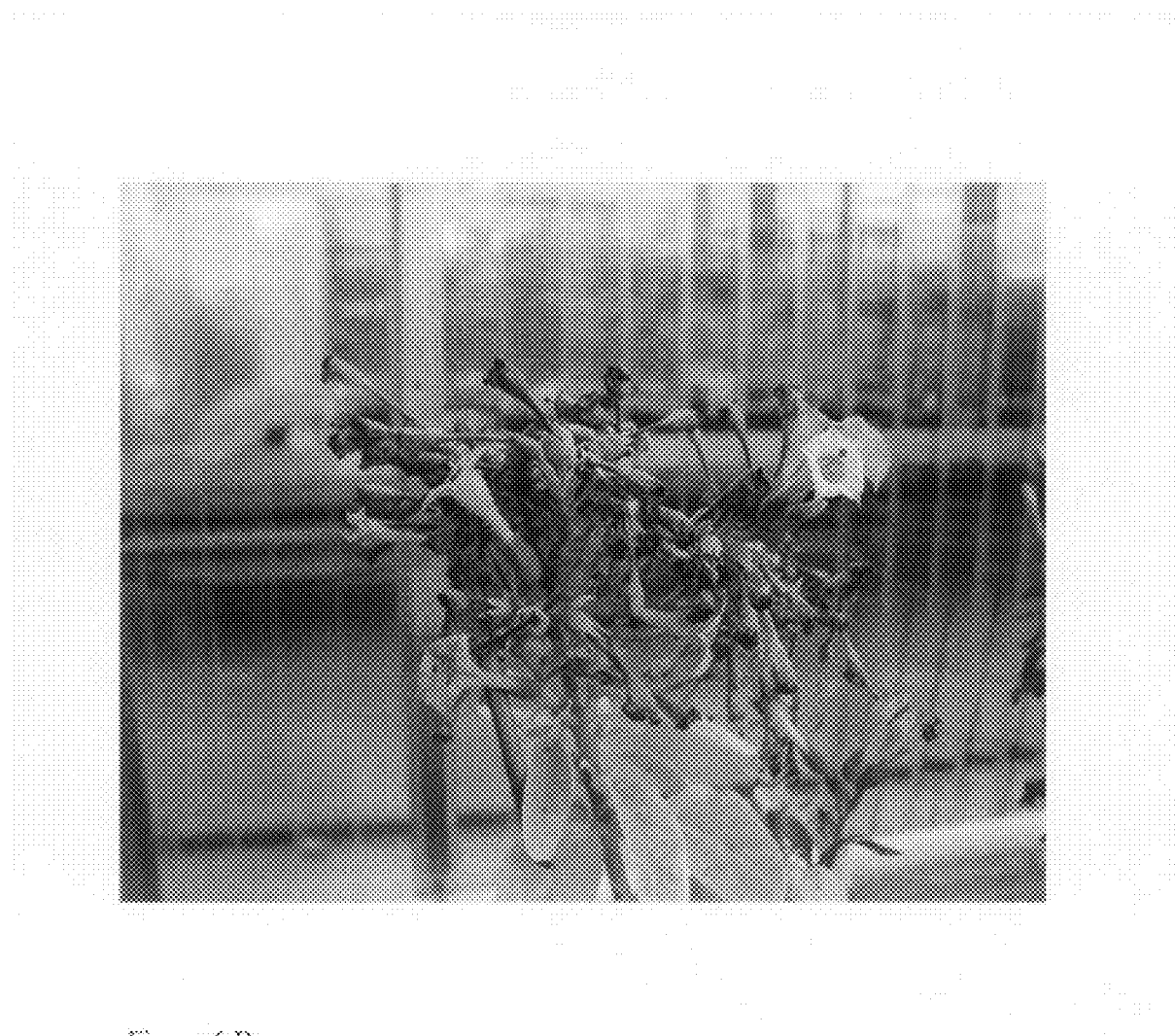
Figure 6:

GUS positive pVK31+HSp-barstar transgenic lines exhibiting normal phenotype formed normal flowers, which however dried without forming fruits in ambient temperature (FIG. 6B). Heat shock treatment of the plants at 42° C. for 1-2 hours for every second day during flowering and seed maturation enabled the plants to form fruits and to produce viable seeds (FIG. 6C).

Plants of some transgenic lines were able to form fruits and produce seeds. However, germination capacity of these seeds depended on whether heat shock treatment was applied to parent plant or not. As seen from FIG. 15 seeds from self-pollinated plants did not germinate if the plant was not subjected to heat shock.

EXAMPLE 3

Segregating Double RBF System Efficiently Eliminates Flow of Transgenes when Transgenic Plants Cross with Wild Type Ones. Transgenic Plants having Segregating Double RBF System Show Mendelian Segregation of TGI-BC and of RC.

In order to simulate transgene flow process non transgenic tobacco plants were pollinated with pollen of selected transgenic plants of Example 2.

Germination tests were performed with seeds of self-pollinated transgenic plants and with seeds of plants that were crosses between transgenic and non transgenic plants. The germination tests demonstrated clear Mendelian segregation of the suicidal trait caused by BCs and of the recovering trait caused by RC. This can be well seen from the germination results shown in FIG. 15. About 50% of the seeds of crosses between transgenic line pVK31-5(HSp-10) and non transgenic plants germinated without heat shock and 50% were fully unable to germinate. This demonstrates clear segregation of one barnase-containing insert in proportion 1:1 (half of the seeds did not carry the BC nor the TGI linked to it and were able to germinate, while half of the seeds carried the TGI and were dead because they also carried the BC). About ¾ of the seeds of crosses between transgenic line pVK31-5(HSp-10) and non transgenic plants germinated when the parent plant was treated with heat shock at 42° C. 1-2 hours every second day during flowering and seed maturation. This indicates that ¼ of the seeds also carried the RC insert and survived after heat shock, which means that RC inserts also segregated as well as BC-TGI.

FIG. 8 depicts theoretically the hybridization of the segregating double RBF system. Here in F2 hybrids half of the plants carry blocking construct linked to the transgene of interest. Half of these plants are unable to recover because of absence of recovering construct. Therefore, 50% negative selection eliminates the transgene of interest from the natural population.

In practice however, more intensive expression of barnase, as shown in line pVK31-1-(HSp-2) led to death of all self-pollinated seeds in fruit without heat shock treatment. Without heat shock treatment plants that were crosses of transgenic and non transgenic plants of pVK31-1-(HSp-2) line produced also almost exclusively non germinating seeds. Heat shock treatment of these plants resulted in germination of about 97% of the seeds, even if each seed did not carry RC after segregation. This effect of absolute (100%) germination or dying) in hybrid progeny seeds can be explained by easy migration of small Barnase and/or Barstar proteins from embryo to embryo when these proteins are expressed in high enough level.

For one skilled in the art it would be clear that in breeding for practical purposes one should select the lines most desirable for the purpose. In this case it seems that line pVK31-1-(HSp-2) would be more efficient in gene containment purposes.

Expression of the barnases was detected in RT-PCR using primers (SEQ ID NO: 12, 13, 14 and 15) developed for specific sequences in 5' and 3' UTRs different in the barnase genes. Amplified product was sequenced. Each sequence of the both barnase amplificates coincides with DNA sequence in plant transformation vector. Expression of barstar mRNA was analyzed with Northern and was found to be similar to described in Example 6 and shown in FIG. 7C.

EXAMPLE 4

Transgenic Plants Having the Segregating Double RBF System Consisting of Two Similar Barnase Coding Sequences (Barnase 1) Under Different Promoters and UTRs, and RC in Another Insert Consisting of Barstar Gene Under 35S Promoter

*Eschericia coli* strain XL1 was used for cloning of the DNA constructs. Tobacco plants (*Nicotiana tabacum* cv. Samsung) were transformed by *Agrobacterium tumefaciens* strain LB4404 carrying pGPTV-KAN vector having the RC which in this example was a barstar coding sequence (SEQ ID NO: 3) driven by 35S promoter. Putative transformants were selected on 75 mg/l kanamycin. Plants that were positive in Northern analysis against barstar probe were chosen for second transformation with pVK31 (pGPTV-HPT/pBIN19-based) vector carrying the TGI (GUS in this example). Putative transformants were selected on 60 mg/l hygromycin. The TGI was placed in between of two BCs expressing the same coding sequence of barnase (SEQ ID NO: 1) under different promoters as shown in FIG. 1A. Tobacco shoots that recovered on hygromycin selection were analyzed in histological GUS assay. GUS-positive plants were transferred from in vitro culture to the greenhouse for further studies.

As expected the transgenic tobacco plants double-transformed with pVK31+35Sp-barstar vectors did not show barnase-suffering phenotype, because barstar was constitutively expressed under 35Sp. Barstar-RNA and GUS positive lines produced seeds normally.

The pVK31+35Sp-barstar lines expressed barstar RNA constitutively at level of 0.3-0.5 pg/µg of total RNA. According to Northern analysis barnase RNA was expressed in embryo at the level of 0.02-0.05 pg/µg of total RNA. Expression of the barnases was detected separately in RT-PCR using primers (SEQ ID NO: 12, 13, 14 and 15) developed for specific sequences in 5' and 3' UTRs different in the barnase genes. Amplified product was sequenced. Each sequence of the both barnase amplificates coincides with DNA sequence in plant transformation vector.

Germination Tests

In order to simulate transgene flow process non transgenic tobacco plants were pollinated with pollen of selected transgenic plants.

Germination tests were performed with transgenic seeds of self-pollinated transgenic plants and that were crosses between transgenic plants and non transgenic plants. FIG. 16 shows the results of the germination tests.

Several lines like pVK31-1 (35Sp 5) and pVK31-3 (35Sp 6) demonstrated segregation of RC from the BCs (FIG. 16). Average proportions of germinated and non germinated seeds are close to Mendelian segregation of one BC and two RC independent inserts. When the transgenic plants carry one BC-TGI-BC insert and two independent RC inserts they would segregate so that self-pollinated seed population would have ¾ seeds containing BC and only ¹⁄₁₆ would be free of RC. This segregation would result in proportion of germinating seeds to non-germinating as to 20:1 as is the case with line pVK31 3 (35Sp 6) (FIG. 16). Plants being crosses between transgenic and non transgenic parents would produce seeds containing these inserts segregating in proportion of ½ of the seeds with BC and ¾ of the seeds carrying either one or two RCs. Thus the proportion of germinated to non-germinated crossed seeds would be 7:1. This is the case in line pVK31 3 (35Sp 6).

These proportions could be changed by effect of high expression of BC or RC as is seen in line pVK31-1 (35Sp 5) (FIG. 16). To one skilled in the art it would be clear that for practical breeding purposes the best transgenic lines for the ultimate purpose need to be selected.

Germination assays on tobacco seeds carrying pVK31+pGPTV-KAN-35Sp-barstar construct. (Abbreviations: NTS—non transgenic tobacco *Nicotiana tabacum* cv. Samsung)

EXAMPLE 5

Transgenic Plants Having the Double RBF Consisting of Two BCs Having Two Different Barnase Coding Sequences (SEQ ID NO: 1 and SEQ ID NO: 2) and an RC in the Same Insert (Single Insert System). Only Systematic Heat Shock Treatment Can Overcame the Effect of Two Blocking Constructs.

*Eschericia coli* strain XL1 was used for cloning of the DNA constructs. Leaf segments of tobacco plants (*Nicotiana tabacum* cv. Samsung) were inoculated with suspension of *A. tumefaciens* strain LBA4404 carrying the pVK34 (pGPTV-HPT/pBIN19-based) binary vector. Putative transformants were selected on 60 mg/l hygromycin. Two BCs and an RC were cloned in the same vector with TGI (35Sp-GUS) and hpt-selectable marker as shown in FIG. 1C and described in Example 1.

Transgenic tobacco plants positive in GUS and Southern analyze were grown in greenhouse in the ambient and in heat shock conditions (42° C. for one hour every second day during flowering and maturation of the seeds). Transgenic lines having normal phenotype were selected for further experiments and analysis.

Phenotypically expression of barnase 2 under CRU promoter reveals as incapability of plant to develop fruits. Flowers on inflorescence dried with ovaries and peduncles after flowering (FIG. 6B). The effect of barnase expression under CRU promoter was removed by application of heat shock (FIG. 6C).

In order to prove that an occasional heat shock is not enough to overcome the blocking effect we subjected some transgenic plants to heat shock for once or for three times. These plants were able to form one or two fruits in inflorescence. However, the seeds were not able to germinate. This shows that although the effect of BC in ovaries was to overcome, the BCs still blocked the germination. Only plants that were systematically subjected to heat shock treatment (42° C. for one hour every second day during flowering and seed maturation) could form germinating seeds. After systematic heat shock treatment the plants produced seeds with germination percentage of 90-95%. About ¾ of the seedlings were GUS positive indicating that they had the single transgenic insert.

Non transgenic plants that were pollinated with transgenic pollen produced normal seeds with germination percentage close to 100% when the plants were subjected to heat shock treatments. Half of these seedlings were GUS positive indicating they carried the transgenic insert. Some of the GUS positive seedlings of the second generation were grown to mature plants. The plants exhibited the same phenotypic traits as the parental plants producing germinating seeds only after the heat shock treatment.

Without heat shock the pollinated non transgenic tobacco plants produced seeds with germination percentage of only 50%. Usually none of the germinated seedlings were GUS positive, indicating that they were non transgenic. A few of the seedlings that were GUS positive suffered of reduced growth.

EXAMPLE 6

Barnasel driven by CRU promoter is responsible for the symptoms of dried flowers. Both barnase genes are expressed in double RBF plants. One RC expression titer is enough to recover double titer of two BCs.

Phenotypically expression of barnase2 under Cru promoter reveals as incapability of plant to develop fruits. Flowers in inflorescence dried with ovaries and peduncles after flowering (FIG. 6B). This effect was detected both in the plants carrying double RBF of pVK34 insert (FIG. 1C) as well as single RBF of pVK35 construct (FIG. 1D). The effect of barnase expression under CRU promoter was removable by application of heat shock (FIG. 6C). Because the single RBF in pVK35 lines caused the dried flowers symptom the BC2 was particularly responsible for this phenomenon specified by expression of CRU promoter. The phenotypical effect of barnase expression was also similar in segregating and one insert double RBF systems.

Figure 3:
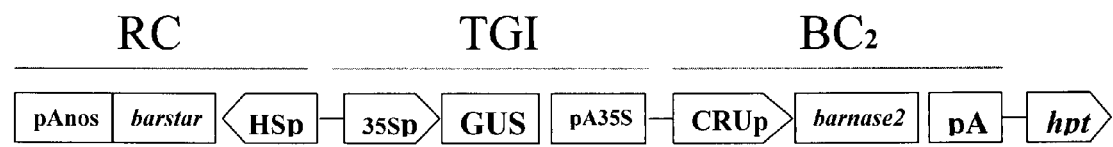
FIG. 3 depicts a single RBF with BC2 driven by CRU promoter. pVK35 plant transformation vector is identical to pVK34 except that BC1 containing SH-EPp-barnase-pAnos is removed from the vector.

Plants positive in the GUS assay (i.e. having the TGI) and exhibiting biological effect of barnase and barstar expression were analyzed in Northern analysis and Real-Time PCR. RNA was isolated from heat shock treated embryos of pVK34 lines carrying double RBF and pVK35 lines carrying single RBF (high-TA barnase). To show that both the barnase genes were expressed in the double RBF the total RNA samples were hybridized with probes developed for barnase1 (FIG. 3A). One lane with 10 pg of synthetic barnase2 was added to the blot in order to measure cross-hybridization signal with barnase2. The signal from barnase2 did not exceed 3% of signal of tested barnase1. The analogous Northern was performed with barnase2 (FIG. 3B). The level of expression of BC, barnase1 in embryos achieved 0.05 pg/μg of total RNA. Barnase2 was expressed up to 0.03 pg/μg of embryo total RNA.

RT-PCR analysis showed that both types of barnase mRNAs are present in the embryo total RNA. Sequencing of amplified product confirmed that the particular coding regions of BC1 and BC2 coincide with the mRNA of barnases. Real-Time PCR analysis was performed on embryo and ovary total RNA of pVK34 lines. Level of expression of both of the barnases ranged from $0.25 \times 10^9$ molecules to $17.5 \times 10^9$ molecules per pg of total RNA. The result of the analysis indicated that level of barnase1 mRNA in embryos was twice as high as in ovaries. In contrast, level of expression of barnase2 was 2-4 times higher in ovaries than in embryos. This data supports the fact that barnase2 driven by CRU promoter was responsible for the symptom of dried flowers in tobaccos carrying pVK34 construct. It also coincided with the same biological symptom of dried flowers in pVK35 lines carrying single $BC_2$ (CRUp-barnase2).

Figure 7:
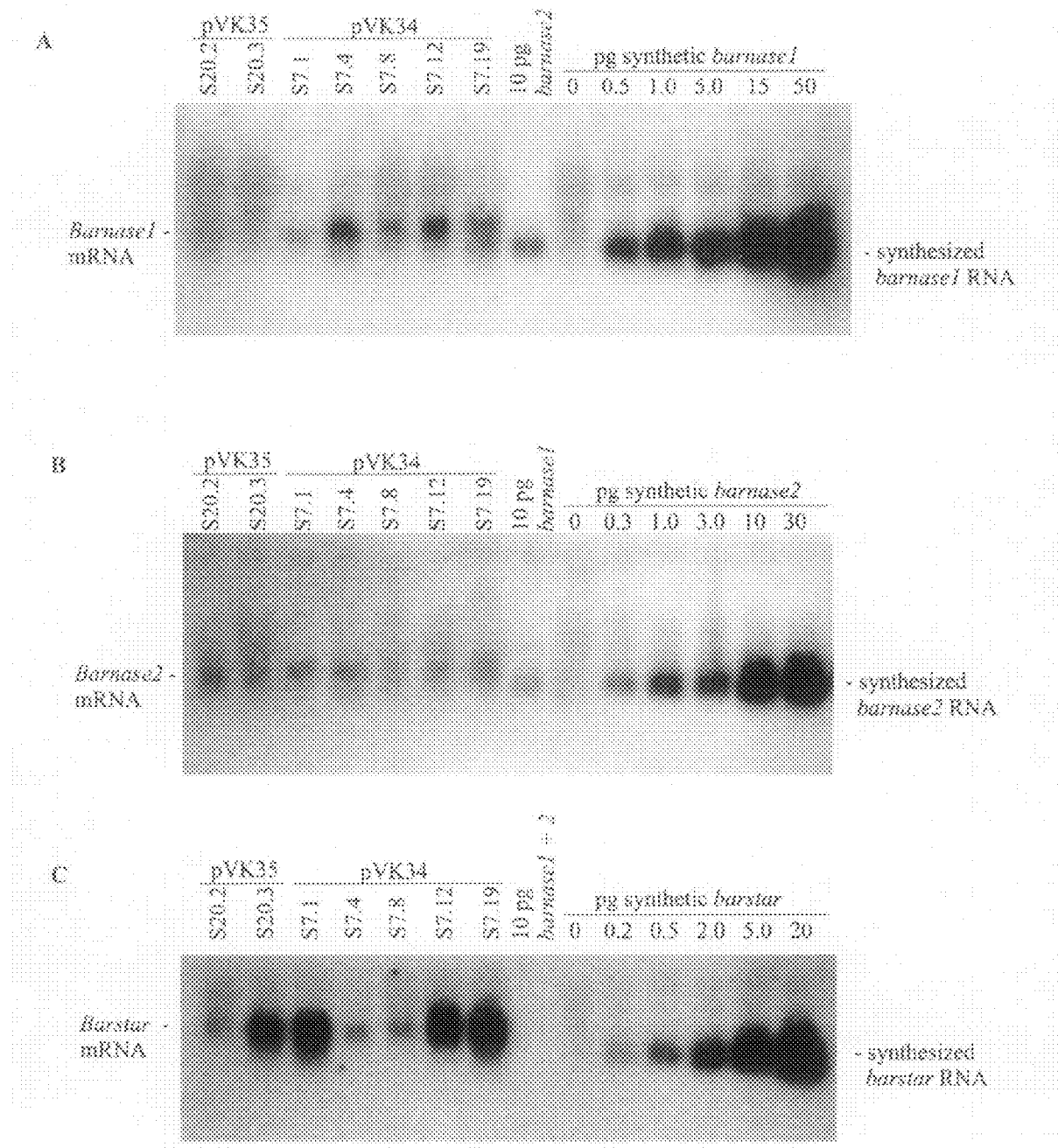
FIG. 7 Northern analysis of expression of barnase1 with enriched GC-content (BC1) and barnase2 with enriched AT-content (BC2), and barstar (RC) in embryos of heat shock treated tobacco plants carrying the double (pVK34) or single (pvK35) RBF construct.

The expression level of heat induced barstar mRNA achieved 1.0 pg/μg of total embryo RNA. This is about 10 times higher than expression of any barnases (FIG. 7). Therefore the molecular data confirmed the phenotypical data, i.e. one RC expression titer was enough to recover double titer of two BCs (FIG. 7C).

It will be clear to those having skill in the art that many changes may be made in the above-described details of preferred embodiments of the present invention without departing from the underlying principles thereof. The scope of the present invention should therefore be determined only by the following claims.

EXAMPLE 7

Double RBF System, in which TGI (GUS) is in Between of two BCs Both of which Contain a Blocking Sequence Coding for a Different Genes: Barnase and Phytoene Synthase. Promoters of BC Contain TetR Repressor Binding Sequence (tetO-tet Operator) and One RC Encoding Repressor Protein (TetR in this Example).

BCs flank the TGI and RC as shown in FIG. 9. $BC_1$ consists of crtB gene (SEQ ID NO: 5) from *Erwinia uredovora* (Shewmaker, et al., Plant J., 20:401-412, 1999) encoding for Phytoene synthase and driven by SH-EP promoter. $BC_2$ consists of barnase gene driven by CRU promoter. The SH-EP and CRU promoters have modified 3' end, in which the vicinity of TATA boxes (SEQ ID NO: 8) are changed as shown in SEQ ID NO: 9 and SEQ ID NO: 10, respectively: three tet operators from Tn10. RC consists of TetR gene of SEQ ID NO: 16 driven by Heat Shock promoter.

Phytoene synthase ($BC_1$) expresses in embryos and germinating seeds and redirects metabolites from the gibberellin pathway and enhances synthesis of the carotene precursor pigment phytoene and consequently carotenoids. The enhanced carotenoid synthesis leads to incapability of germinating seeds to growth and photosynthesize. Morphologically sprouts look yellow-orange in color and can not grow further than to the stage of cotyledon expansion (as shown on FIG. 10). Barnase ($BC_2$) digests RNA molecules in the embryos, when it is expressing under CRU promoter. The expression leads to the symptom of dried flowers and incapability of seeds to germinate. Both of the blocking genes express in natural conditions if RC is not activated.

After heat shock application (1-2 hours 42° C. every second day) during flowering/seed maturation and seed germination the seeds are capable to germinate and seedlings to grow further. The heat shock application induces the expression of Tet repressor, which binds the tet operators in the promoters of BCs thereby making the BCs inactive.

EXAMPLE 8

Double RBF System, in which TGI (GUS) is in Between of two BCs Both of Which Contain a Blocking Sequence Coding for Different Genes: Barnase ($BC_1$) and Phytoene Synthase ($BC_2$); $RC_1$ Consists of Barstar Gene Under HSp Promoter; Promoter of $BC_2$ (Phytoene Synthase) Contains TetR Repressor Binding Sequence (tetO-tet Operator) and $RC_2$ Encoding Repressor Protein (TetR in this Example) Under HS Promoter.

BCs flank the TGI and RCs as shown in FIG. 9. $BC_1$ consists of crtB gene (SEQ ID NO: 5) from *Erwinia uredovora* (Shewmaker, et al., Plant J., 20:401-412, 1999) encoding for Phytoene synthase and driven by SH-EP promoter. $BC_2$ consists of barnase gene driven by CRU promoter, which has modified 3' end, in which the vicinity of TATA box (SEQ ID NO:8) is changed as shown in SEQ ID NO: 10: three tet operators (SEQ ID NO:11) from Tn10. $RC_1$ consists of tetR gene (SEQ ID NO: 16) driven by Heat Shock promoter. $RC_2$ consists of barstar gene driven by the Heat Shock promoter.

Phytoene synthase ($BC_1$) expresses in embryos and germinating seeds and redirects metabolites from the gibberellin pathway and enhances synthesis of the carotene precursor pigment phytoene and consequently carotenoids. This leads to incapability of germinating seeds to growth and photosynthesize. Morphologically sprouts look yellow-orange in color and can not grow further the stage of cotyledon expansion (as shown on FIG. 10). Barnase ($BC_2$) digests RNA molecules in the embryos, when it is expressing under CRU promoter. The expression leads to dried flowers symptom and incapability of seeds to germinate. Both the blocking genes express in natural conditions if RCs are not activated.

After heat shock application (1-2 hours 42° C. every second day) during flowering/seed maturation and seed germination the seeds are capable to germinate and seedlings to grow further. The heat shock application induces the expression of Tet repressor in the $RC_1$, which binds the tet operators (SEQ ID NO: 11) in the promoters of BCs. After the binding the promoters of the $BC_1$ becomes inactive. The same heat shock treatment induces the $RC_2$ expressing Barstar, which binds to Barnase and inactivates BC$_2$. Thus, the blocked functions become recovered and plant becomes rescued from suicide.

EXAMPLE 9

Simple RBF without RC: *Brassica napus* Plants Expressing crtB Gene Produce Seeds, which Can Not Germinate Without Recovering Germination by Addition of Gibberelic Acid.

Figure 11:
FIG. 11 depicts transgenic insert (construct) containing simple RBF (crtB gene) and selection marker hpt gene as TGI representative. Blocking construct (BC) consist of crtB gene encoding for phytoene synthase headed by tps pea SSU plastid transit leader. The crtB gene from *Erwinia uredovora* is driven by heat shock promoter (HSp) from *Vicia faba* and ended by nopalin synthase polyadenylation signal. Selection marker—hygromycin phosphatase (hpt) gene driven by 35Sp from CaMV also served as transgene of interest TGI.
Figure 12:
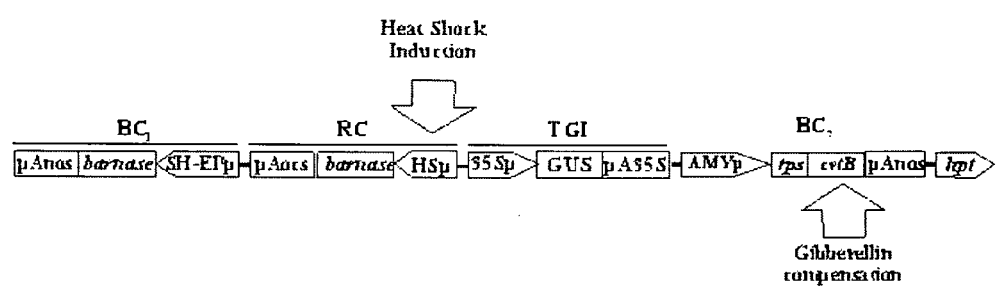
FIG. 12 depicts DNA construct consisting of double RBF, in which one BC (barnase) is recovered by induction of RC (barstar) and another BC (crtB) is recovered by gibberellin and sucrose treatment. $BC_1$ consists of barnase gene expressed under endopeptidase promoter (SH-EPp) and is recovered by RC consisting of barstar gene driven by Heat Shock promoter (HSp). $BC_2$ contains crtB gene under Amylase promoter (AMYp) expressing germination specifically. TGI is represented by GUS gene.

Gene crtB encoding phytoene synthase was cloned by high fidelity PCR from *Erwinia uredovora* (Shewmaker, et al., Plant J., 20:401-412, 1999) (SEQ ID NO:5). The gene was cloned in the plant transformation vector in the construct shown in FIG. 11. The gene was driven under Heat Shock promoter from Soy Been (*Glycine max*). Expressing as heat shock inducible promoter in tobacco plants (as described in the previous examples), HSp exhibits germination (first 3 to 7 days) specificity in oil seed and tobacco plants. In order to target the phytoene synthase into plastids, pea SSU plastid transit leader peptide (Misava et al. 1993, Plant J. 4, 833-840) encoding sequence was attached in front of the CDS. The transit peptide and spacer sequence (Shewmaker, et al., Plant J., 20:401-412, 1999) was back-translated according to *Brassica* plant codon preference (SEQ ID NO:6) and cloned in plant transformation vector as shown in FIG. 11. Selection marker hpt was used as TGI.

Figure 10:
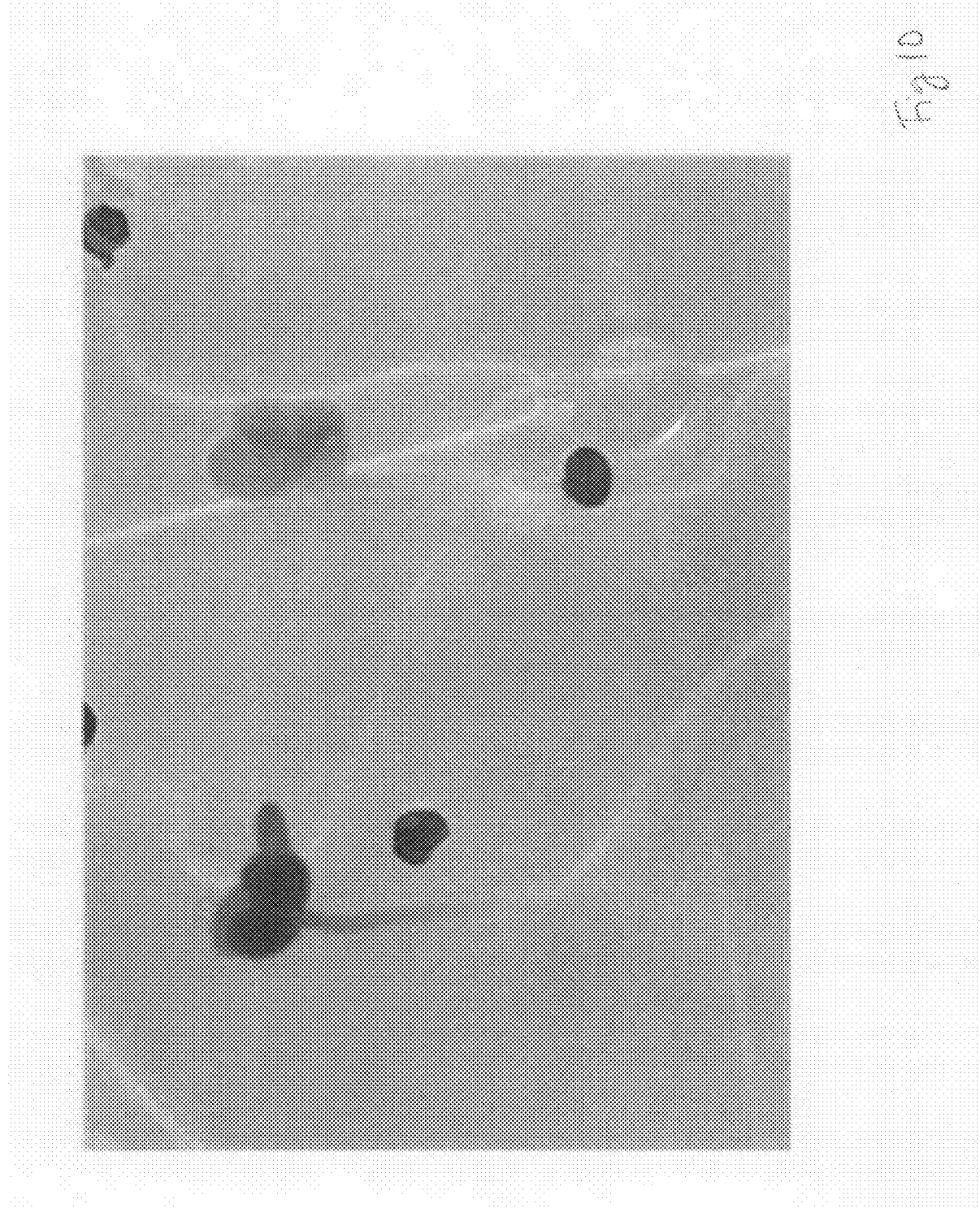
FIG. 10 depicts effect of over expression of crtB gene on Brassica seedlings. Transgenic seedling has yellow/orange color due to overproduction of carotenoids and is incapable of formation the first true leaves. On left—non transgenic control sprout. On right—transgenic sprout.

Hypocotyls of *B. napus* and leaf segments of *N. tabacum* were transformed by *A. tumefaciens* LBA4404 inoculation. Regenerated shoots were selected on hygromycin and checked on transgene in PCR. PCR-positive shoots were grown in the greenhouse and were self-pollinated. Transgenic plants over expressing crtB gene were dwarfish and had yellowish inclusions on leaves. The normal phenotype plants were selected to produce seeds. Transgenic seeds expressing crtB gene developed an orange colored sprouts ('golden sprouts') as shown in FIG. 10. In natural conditions the orange sprouts can not grow further the stage of expanding cotyledons.

Expressing in early germination stage under HSp crtB gene overproduces Phytoene synthase. This enzyme produce carotenoid precursor Phytoene-C$_{40}$ from source molecule Geranylgeranyl diphosphate-C$_{20}$. Geranylgeranyl diphosphate-C$_{20}$ is also precursor for synthesis of chlorophylls, tocopherols and gibberellins (Fray et al., Plant J. 8: 693-701, 1995). Therefore over expressing phytoene synthase depletes the mutual source for synthesis of those molecules. Lack of precursor for chlorophyll together with overproduction of carotenoids led to phenomena of 'golden sprouts'. Lack of gibberellin precursor led to block of germination, because the gibberellin is the essential hormone regulating germination process. crtB gene acted as Blocking Construct in the germinating seeds by decreasing the content of gibberellin. Therefore the transgenic plants can not grow and reproduce in natural conditions.

Figure 14:
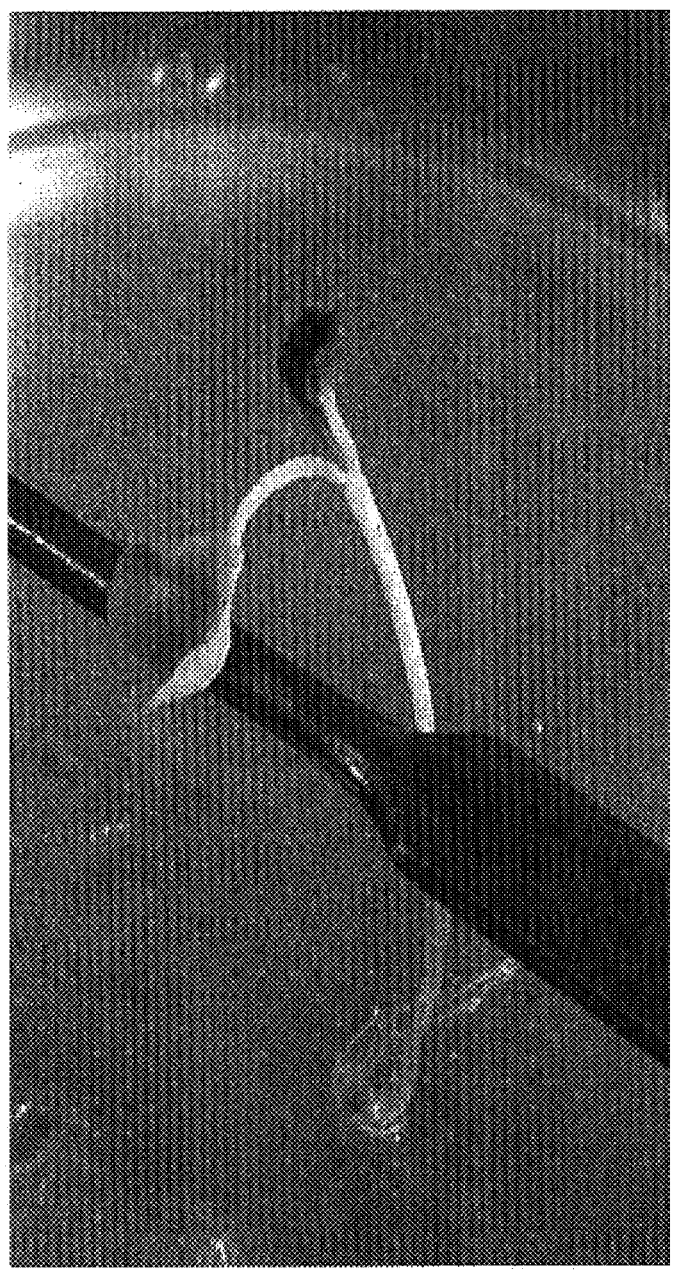
FIG. 14 shows a transgenic *Brassica* sprout carrying crtB containing RBF construct growing on medium containing gibberellin (10 mg/l $GA_3$) and sucrose (2%). Addition of gibberellin and sucrose has overcome the block by crtB gene expression and the first emerging leaves are green.

To demonstrate action of the RBF germination tests were performed. To recover germination function, external gibberellins and sucrose were applied in different concentrations. Seeds were sterilized in Na-hypochlorite seeds and thereafter germinated on Murashige Skoog (MS) agarose media. Golden sprouts could not expand cotyledons on media without sucrose and GA$_3$ (gibberelic acid). Addition of 2% sucrose increased the growth rate and size of sprouts to double. Sprouts developed to full sized cotyledons but could not produce the first leaves. GA$_3$ had not effect on the sprouts until concentration 1 mg/l. 50 mg/l GA$_3$ blocked germination of non-transgenic sprouts. Golden sprouts could germinate but need also transfer onto MS without gibberellin in 3-7 days after start of germination to continue germination. On MS media supplemented with 2% sucrose and 10 mg/l GA$_3$ transgenic sprouts produced the first green leaves overcoming blocked germination (FIG. 14). Gibberellic acid alone, without sucrose addition was unable to recover the germination function. Therefore, recovery of the block of germination due to expression of crtB gene was enabled only by addition of sucrose and gibberellic acid in combination. Thus, the external intervention in this case was addition of sucrose and gibberellic acid. Optimal conditions for the transgenic *B. napus* seedlings were 2% sucrose and 5-10 mg/l GA$_3$.

Figure 13:
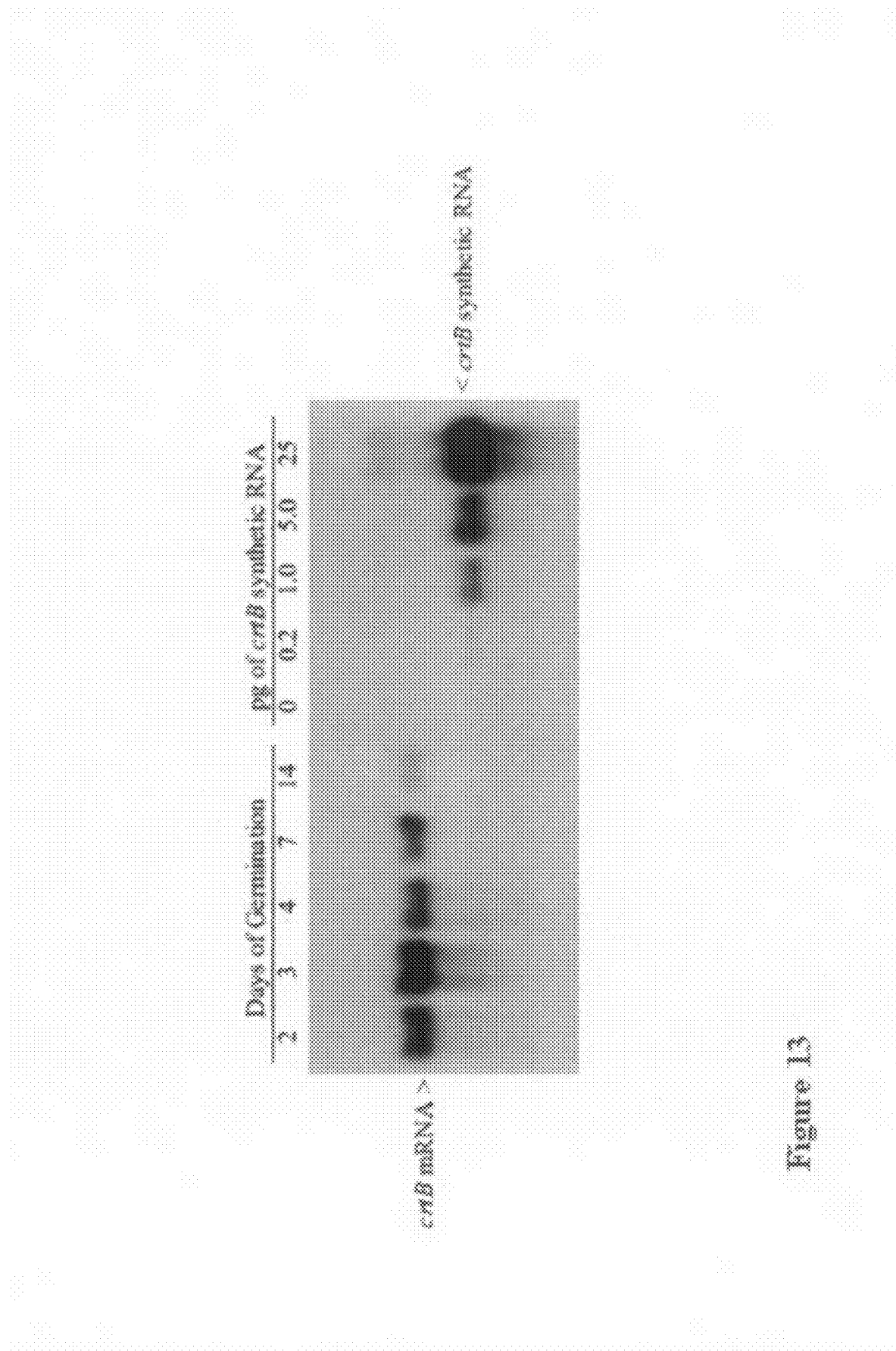
FIG. 13 shows expression of crtB gene in sprouts of *B. napus*. 1 μg of total *B. napus* sprout RNA was loaded in each lane. Control cold synthetic RNA was mixed with 1 μg of non transgenic carrier RNA. The synthetic RNA of crtB gene was shorter than mRNA because of absence of polyA tail. Expression of crtB gene achieved peek of expression 7 pg in 1 μg of total RNA on the third day of germination and faded to 0.3 μg after two weeks.

Expression of crtB gene was detected in Northern analysis from seedlings of *B. napus* of different ages. (FIG. 13). The transgenic seeds were sterilized in 2% Na hypclorite and germinated aseptically on MS (Murashige-Skoog) agar. The 'golden sprouts' were collected in 2, 3, 4, 7 and 14 days of germination. Total RNA was isolated as described above. The samples were run in agarose gel and hybridized with Digoxgenin RNA probe developed to crtB gene. The expression of the crtB mRNA was compared to synthetic cold RNA loaded in the same ge/blot in different amounts. The expression of phytoene synthase mRNA increased from 1 pg/µg of total RNA at the second day up to 4 pg/µg at the fourth day of germination. After that crtB expression continued one week and faded after about two weeks.

EXAMPLE 10

Double RBF System, in which TGI (GUS) is in Between of two BCs Containing Different Blocking Genes: Barnase and Phytoene Synthase. The System contains only one RC which encodes barstar gene under Heat Shock promoter. Recovery of phytoene synthase action is performed by gibberellin treatment.

Genetic construct contains GUS gene as TGI, barnase as BC$_1$, barstar gene as RC, crtB gene as BC$_2$ and selection marker hpt gene. Positions of the genes are shown in the FIG. 12. Transgenic plants can not produce germinating seeds in normal conditions. To reproduce normally the plants needs heat shock treatment (42° C. 1-2 hours in each second day) during fruit maturation and gibberellin-sucrose support during germination.

What is claimed is:

1. A method for molecular control of gene containment in sexually reproducing transgenic plants by providing a plant with a recoverable block of function (RBF) system, said system comprising:
   a first blocking construct (BC1) and a second blocking construct (BC2), said blocking constructs having a capacity to block at least one molecular or physiological function essential for development or reproduction of the transgenic plant, thereby leading to death or incapacity of sexual reproduction, said blocking constructs each comprising a blocking gene driven by an embryo-or germination specific promoter, said blocking gene being isolated and purified or artificial, and coding for Barnase protein;
   a transgene of interest (TGI) encoding desired gene products, said TGI being isolated and purified or artificial gene further being inserted between said two BCs; and
   a means to recover the functions blocked by the BCs, said means comprising at least one recovering construct (RC) comprising a recovering gene encoding for Barstar protein, said RC locating in a different chromosome apart from said BCs and said TGI and being capable to recover the blocked functions under homozygous condition introduced by intraline hybridization.

2. The method according to claim 1, wherein the at least one RC is driven by a constitutive promoter.

3. The method according to claim 2, wherein the constitutive promoter is CaM 35S promoter.

4. The method according to claim 1, wherein the blocking genes of the two BCs code for same mRNA.

5. The method according to claim 4, wherein each of the blocking genes code for Barnase, said blocking genes being further driven by two different germination/embryo development specific promoters; and
   the means to recover consists of one RC, said RC comprising a sequence coding for Barstar protein and said Barstar coding sequence further being driven by a constitutive promoter.

6. The method according to claim 5, wherein the germination/embryo specific promoters are cysteine endopeptidase (SH-EP) promoter and cruciferin (CRU) promoter and the promoter driving the Barstar coding gene is CaMV 35S promoter.

7. The method according to claim 1, wherein the blocking genes of the two BCs have different coding sequences.

8. The method according to claim 7, wherein the first BC comprises an AT enriched Barnase coding gene and the second BC comprises a GC enriched Barnase coding gene.

9. The method according to claim 8, wherein the coding sequences of the blocking genes are according to SEQ ID NO: 1 and SEQ ID NO: 2.

10. A kit for providing gene containment in sexually reproducing transgenic plants said kit comprising:
    a first blocking construct (BC1) and a second blocking construct (BC2), said blocking constructs having a capacity to block at least one molecular or physiological function essential for development or reproduction of the transgenic plant, thereby leading to death or incapacity of sexual reproduction, said blocking constructs each comprising a blocking gene driven by an embryo- or germination specific promoter, said blocking gene coding for Barnase protein;
    a place for inserting a transgene of interest (TGI) encoding desired gene product between the two BCs, and optionally said TGI; and
    a means to recover the functions blocked by the BCs, said means comprising at least one recovering construct (RC) comprising a recovering gene coding for Barstar protein, said RC locating in a different insert than the BCs and instructions for recovery of the blocked function by maintenance of homozygosity by intraline hybridization.

11. The kit according to claim 10, wherein the at least one RC is driven by a constitutive promoter.

12. The kit according to claim 11, wherein the constitutive promoter is CaMV 35S promoter.

13. The kit according to claim 10, wherein the blocking genes of the two BCs code for same mRNA.

14. The kit according to claim 13, wherein the blocking genes are driven by two different germination/embryo development specific promoters and the Barstar coding gene is driven by a constitutive promoter.

15. The kit according to claim 14, wherein the germination/embryo specific promoters are SH-EP promoter and CRU promoter and the promoter driving the Barstar coding gene is CaMV 35S promoter.

16. The kit according to claim 10, wherein the blocking genes of the two Blocking constructs have different coding sequences.

17. The kit according to claim 16, wherein the first BC comprises an AT enriched Barnase coding gene and the second BC comprises a GC enriched Barnase coding gene.

18. The kit according to claim 17, wherein the coding sequences for the blocking genes are according to SEQ ID NO: 1 and SEQ ID NO: 2.

19. A cloning vector system comprising:

a first insert comprising a first blocking construct (BC1) and a second blocking construct (BC2), said blocking constructs having a capacity to block at least one molecular or physiological function essential for development or reproduction of the transgenic plant, thereby leading to death or incapacity of sexual reproduction, said blocking constructs each comprising a blocking gene and driven by- an embryo- or germination specific promoter, and said blocking genes coding for Barnase protein and said first insert further having a place between the two BCs to insert a transgene of interest (TGI) encoding desired gene products therein; and;

a second insert comprising at least one recovering construct (RC) comprising a recovering gene coding for Barstar-protein, said RC being capable to recover the functions blocked by the BCs in the first insert under homozygous condition introduced by intraline hybridization.

* * * * *